United States Patent
Yang et al.

(10) Patent No.: US 10,201,269 B2
(45) Date of Patent: Feb. 12, 2019

(54) APPARATUS AND METHOD FOR REPROCESSING A MEDICAL DEVICE

(71) Applicant: ETHICON, INC., Somerville, NJ (US)

(72) Inventors: Sungwook Yang, Los Angeles, CA (US); Dang Minh Ngo, Fountain Valley, CA (US)

(73) Assignee: Ethicon, Inc., Somerville, NJ (US)

( * ) Notice: Subject to any disclaimer, the term of this patent is extended or adjusted under 35 U.S.C. 154(b) by 65 days.

(21) Appl. No.: 15/157,800

(22) Filed: May 18, 2016

(65) Prior Publication Data
US 2017/0332892 A1 Nov. 23, 2017

(51) Int. Cl.
*A61B 1/12* (2006.01)
*A61L 2/16* (2006.01)
(Continued)

(52) U.S. Cl.
CPC .............. *A61B 1/125* (2013.01); *A61B 1/123* (2013.01); *A61L 2/16* (2013.01); *A61L 2/18* (2013.01); *A61L 2/24* (2013.01); *B08B 3/08* (2013.01); *B08B 3/10* (2013.01); *B08B 3/102* (2013.01); *B08B 3/14* (2013.01); *B08B 9/023* (2013.01);
(Continued)

(58) Field of Classification Search
CPC ... A61B 1/123; A61B 1/125; A61B 2090/701; A61L 2/16; A61L 2/18; A61L 2/24; A61L 2202/24; B08B 3/08; B08B 3/10; B08B 3/102; B08B 3/14; B08B 9/023; B08B 9/0323; B08B 9/0325; B08B 9/0328
See application file for complete search history.

(56) References Cited

U.S. PATENT DOCUMENTS

| 6,986,736 B2 | 1/2006 | Williams et al. |
| 7,479,257 B2 | 1/2009 | Nguyen et al. |

(Continued)

FOREIGN PATENT DOCUMENTS

| EP | 1 707 221 A1 | 10/2006 |
| EP | 1 757 313 A1 | 2/2007 |

(Continued)

OTHER PUBLICATIONS

U.S. Appl. No. 15/157,650, filed May 18, 2016.
U.S. Appl. No. 15/157,952, filed May 18, 2016.
European Search Report, Partial, and Written Opinion dated Mar. 28, 2018 for Application No. EP 17171448.8, 14 pgs.

*Primary Examiner* — Timothy C Cleveland
(74) *Attorney, Agent, or Firm* — Frost Brown Todd LLC

(57) ABSTRACT

An apparatus and method for reprocessing a medical device includes a decontamination basin, a first flush conduit, a second flush conduit, and a manifold. The first and second flush conduits have respective first and second coupling ports configured to fluidly connect to the medical device positioned within the decontamination basin. The manifold is fluidly connected to the first and second flush conduits and configured to distribute the fluid received therein accordingly. The apparatus also includes a first valve, a second valve, and a primary pump configured to discharge the fluid into the manifold at a predetermined supply flow rate. The first and second valve are positioned respectively in the first and second flush conduits for balancing the respective flow rates discharged therefrom at a first predetermined conduit flow rate and a second predetermined conduit flow rate.

20 Claims, 8 Drawing Sheets

(51) Int. Cl.
*A61L 2/24* (2006.01)
*B08B 3/08* (2006.01)
*B08B 3/10* (2006.01)
*B08B 3/14* (2006.01)
*B08B 9/023* (2006.01)
*B08B 9/032* (2006.01)
*A61L 2/18* (2006.01)
*A61B 90/70* (2016.01)

(52) U.S. Cl.
CPC .......... *B08B 9/0323* (2013.01); *B08B 9/0325* (2013.01); *B08B 9/0328* (2013.01); *A61B 2090/701* (2016.02)

(56) References Cited

U.S. PATENT DOCUMENTS

| | | |
|---|---|---|
| 7,686,761 B2 | 3/2010 | Jackson et al. |
| 7,901,349 B2 * | 3/2011 | Feld .................. A61B 1/00057 600/117 |
| 8,246,909 B2 | 8/2012 | Williams et al. |
| 2009/0220377 A1 | 9/2009 | Hasegawa et al. |

FOREIGN PATENT DOCUMENTS

| | | |
|---|---|---|
| EP | 1 769 721 A1 | 4/2007 |
| EP | 3 245 939 A2 | 11/2017 |
| WO | WO 2007/089358 A2 | 8/2007 |
| WO | WO 2009/032644 A2 | 3/2009 |
| WO | WO 2013/059455 A1 | 4/2013 |

* cited by examiner

APPARATUS AND METHOD FOR REPROCESSING A MEDICAL DEVICE

BACKGROUND

The below discussion relates to the reprocessing (i.e., decontamination) of endoscopes and other instruments that are used in medical procedures. In particular, the below discussion relates to an apparatus and a method that may be used to reprocess a medical device, such as an endoscope, after the medical device has been used in a first medical procedure, such that the medical device may be safely used in a subsequent medical procedure. While the below discussion will speak mainly in terms of an endoscope, it should be understood that the discussion may also equally apply to certain other medical devices.

An endoscope may have one or more working channels or lumens extending along at least a portion of the length of the endoscope. Such channels may be configured to provide a pathway for passage of other medical devices, etc., into an anatomical region within a patient. These channels may be difficult to clean and/or disinfect using certain primitive cleaning and/or disinfecting techniques. Thus, the endoscope may be placed in a reprocessing system that is particularly configured to clean endoscopes, including the channels within endoscopes. Such an endoscope reprocessing system may wash and disinfect the endoscope. Such an endoscope reprocessing system may include a basin that is configured to receive the endoscope, with a pump that flows cleaning fluids over the exterior of the endoscope within the basin. The system may also include ports that couple with the working channels of the endoscope and associated pumps that flow cleaning fluids through the working channels of the endoscope. The process executed by such a dedicated endoscope reprocessing system may include a detergent washing cycle, followed by a rinsing cycle, followed by a sterilization or disinfection cycle, followed by another rinsing cycle. The sterilization or disinfection cycle may employ disinfection solution and water rinses. The process may optionally include an alcohol flush to aid displacement of water. A rinsing cycle may be followed by an air flush for drying and storage.

Examples of systems and methods that may be used to reprocess a used endoscope are described in U.S. Pat. No. 6,986,736, entitled "Automated Endoscope Reprocessor Connection with Integrity Testing," issued Jan. 17, 2006, the disclosure of which is incorporated by reference herein; U.S. Pat. No. 7,479,257, entitled "Automated Endoscope Reprocessor Solution Testing," issued Jan. 20, 2009, the disclosure of which is incorporated by reference herein; U.S. Pat. No. 7,686,761, entitled "Method of Detecting Proper Connection of an Endoscope to an Endoscope Reprocessor," issued Mar. 30, 2010, the disclosure of which is incorporated by reference herein; and U.S. Pat. No. 8,246,909, entitled "Automated Endoscope Reprocessor Germicide Concentration Monitoring System and Method," issued Aug. 21, 2012, the disclosure of which is incorporated by reference herein. An example of a commercially available endoscope reprocessing system is the EVOTECH® Endoscope Cleaner and Reprocessor (ECR) by Advanced Sterilization Products of Irvine, Calif.

While a variety of systems and methods have been made and used to reprocess medical devices, it is believed that no one prior to the inventor(s) has made or used the technology as described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
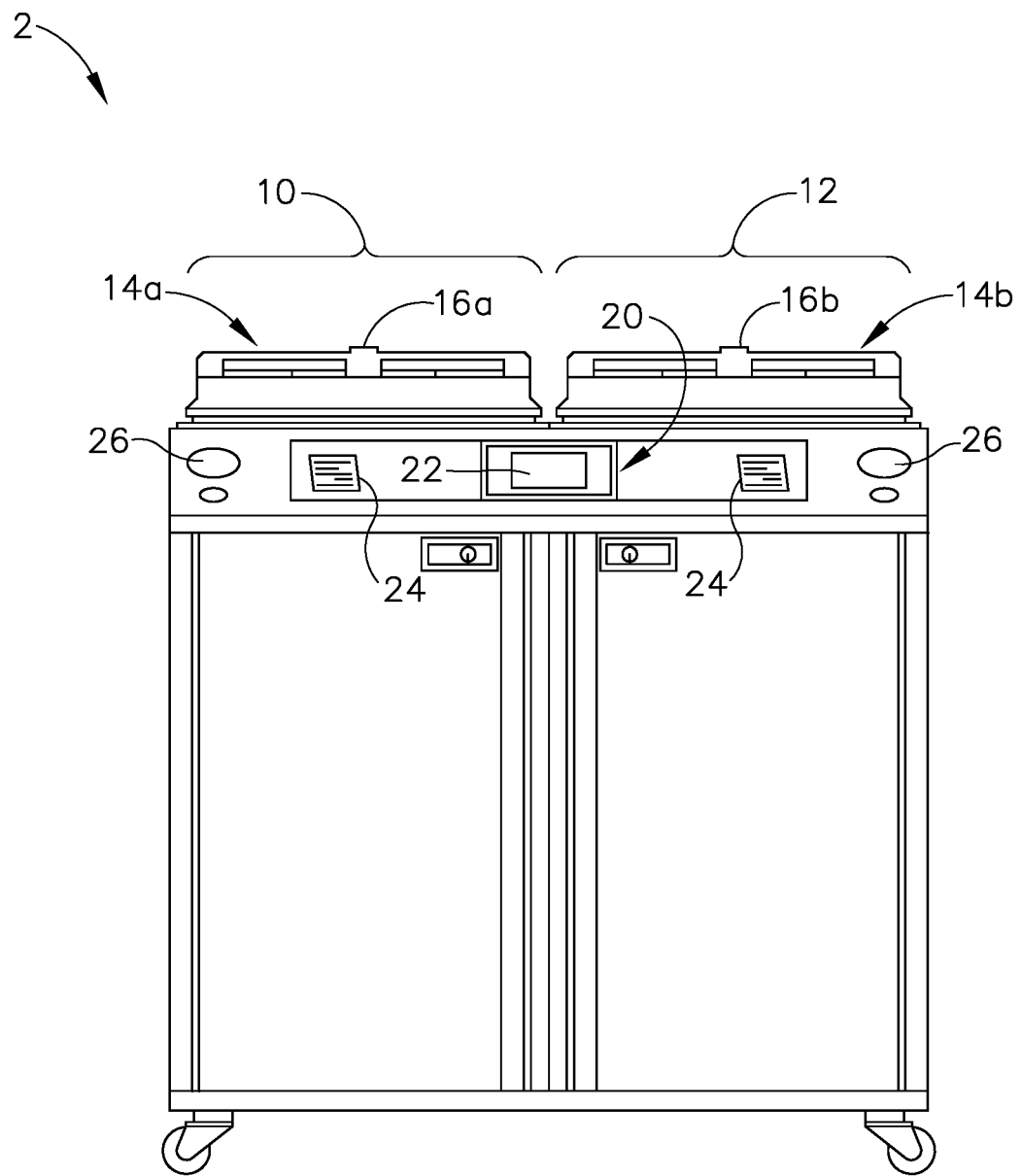
FIG. 1 depicts a front elevational view of a first exemplary reprocessing system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Medical Device Reprocessing Apparatus

Figure 2:
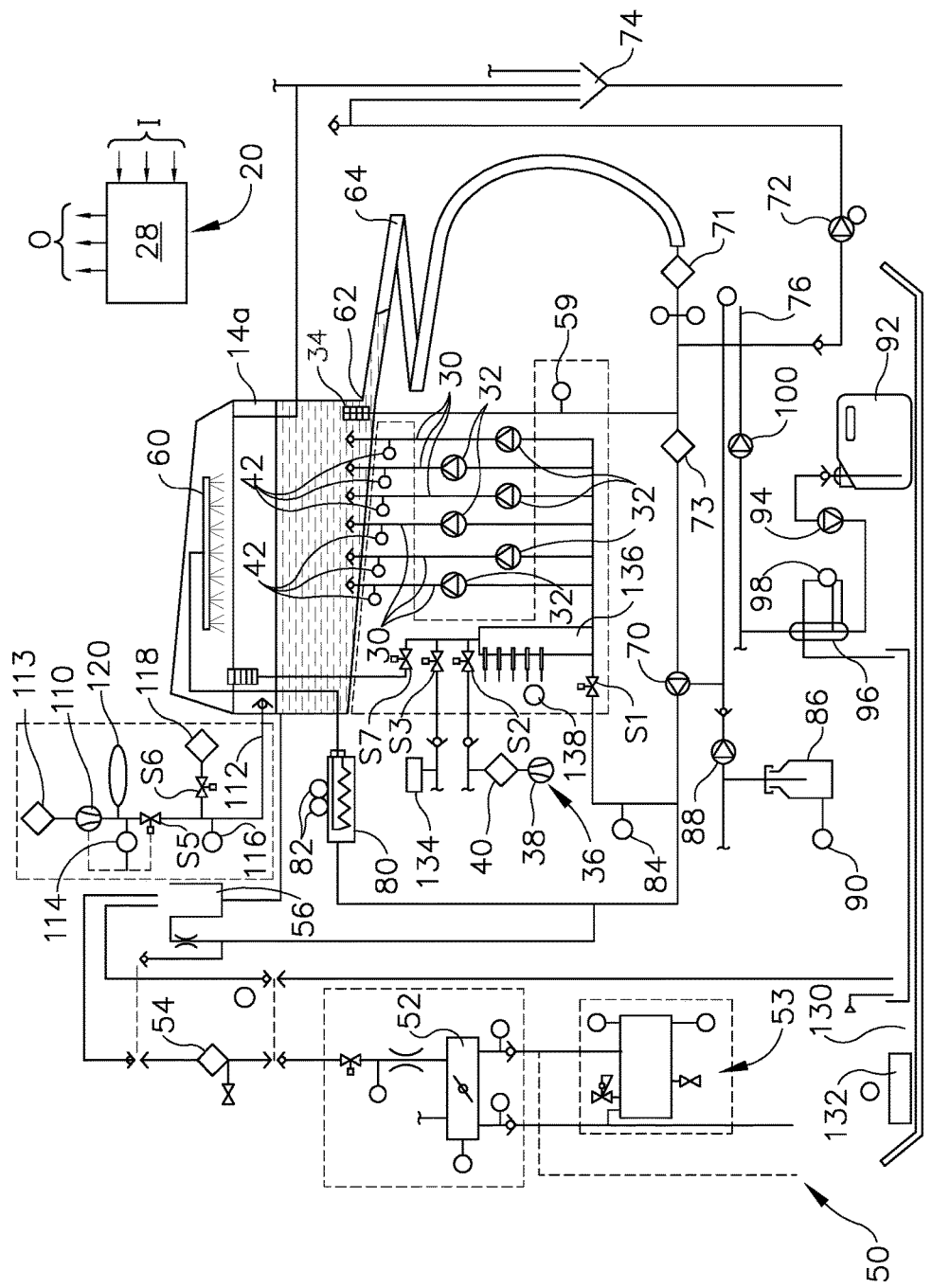
FIG. 2 depicts a schematic diagram of the reprocessing system of FIG. 1, with only a single decontamination basin shown for clarity.

FIGS. 1-2 show an exemplary reprocessing system (2) that may be used to decontaminate endoscopes and other medical devices that include channels or lumens formed therethrough. System (2) of this example generally includes a first station (10) and a second station (12). Stations (10, 12) are at least substantially similar in all respects to provide for the decontamination of two different medical devices simultaneously or in series. First and second decontamination basins (14*a*, 14*b*) receive the contaminated devices. Each basin (14*a*, 14*b*) is selectively sealed by a respective lid (16*a*, 16*b*). In the present example, lids (16*a*, 16*b*) cooperate with respective basins (14*a*, 14*b*) to provide a microbe-blocking relationship to prevent the entrance of environmental microbes into basins (14*a*, 14*b*) during decontamination operations. By way of example only, lids (16*a*, 16*b*) may include a microbe removal or HEPA air filter formed therein for venting.

A control system (20) includes one or more microcontrollers, such as a programmable logic controller (PLC), for controlling decontamination and user interface operations. Although one control system (20) is shown herein as controlling both decontamination stations (10, 12), those skilled in the art will recognize that each station (10, 12) can include a dedicated control system. A visual display (22) displays decontamination parameters and machine conditions for an operator, and at least one printer (24) prints a hard copy output of the decontamination parameters for a record to be filed or attached to the decontaminated device or its storage packaging. It should be understood that printer (24) is merely optional. In some versions, visual display (22) is combined with a touch screen input device. In addition or in the alternative, a keypad and/or other user input feature is provided for input of decontamination process parameters and for machine control. Other visual gauges (26) such as pressure meters and the like provide digital or analog output of decontamination or medical device leak testing data.

FIG. 2 diagrammatically illustrates just one decontamination station (10) of reprocessing system (2), but those skilled in the art will recognize that decontamination station (12) may be configured and operable just like decontamination station (10). It should also be understood that reprocessing system (2) may be provided with just one single decontamination station (10, 12) or more than two decontamination stations (10, 12).

Decontamination basin (14*a*) receives an endoscope (200) (see FIG. 3) or other medical device therein for decontamination. Any internal channels of endoscope (200) are connected with flush conduits, such as flush lines (30). Each flush line (30) is connected to an outlet of a corresponding pump (32), such that each flush line (30) has a dedicated pump (32) in this example. Pumps (32) of the present example comprise peristaltic pumps that pump fluid, such as liquid and air, through the flush lines (30) and any internal channels of endoscope (200). Alternatively, any other suitable kind of pump(s) may be used. In the present example, pumps (32) can either draw liquid from basin (14*a*) through a filtered drain (34) and a valve (S1); or draw decontaminated air from an air supply system (36) through a valve (S2). Air supply system (36) of the present example includes a pump (38) and a microbe removal air filter (40) that filters microbes from an incoming air stream.

A pressure switch or sensor (42) is in fluid communication with each flush line (30) for sensing excessive pressure in the flush line. Any excessive pressure or lack of flow sensed may be indicative of a partial or complete blockage (e.g., by bodily tissue or dried bodily fluids) in an endoscope (200) channel to which the relevant flush line (30) is connected. The isolation of each flush line (30) relative to the other flush lines (30) allows the particular blocked channel to be easily identified and isolated, depending upon which sensor (42) senses excessive pressure or lack of flow.

Basin (14*a*) is in fluid communication with a water source (50), such as a utility or tap water connection including hot and cold inlets, and a mixing valve (52) flowing into a break tank (56). A microbe removal filter (54), such as a 0.2 μm or smaller absolute pore size filter, decontaminates the incoming water, which is delivered into break tank (56) through the air gap to prevent backflow. A sensor (59) monitors liquid levels within basin (14*a*). An optional water heater (53) can be provided if an appropriate source of hot water is not available. The condition of filter (54) can be monitored by directly monitoring the flow rate of water therethrough or indirectly by monitoring the basin fill time using a float switch or the like. When the flow rate drops below a select threshold, this indicates a partially clogged filter element that requires replacement.

A basin drain (62) drains liquid from basin (14*a*) through an enlarged helical tube (64) into which elongated portions of endoscope (200) can be inserted. Drain (62) is in fluid communication with a recirculation pump (70) and a drain pump (72). Recirculation pump (70) recirculates liquid from basin drain (62) to a spray nozzle assembly (60), which sprays the liquid into basin (14*a*) and onto endoscope (200). A coarse screen (71) and a fine screen (73) filter out particles in the recirculating fluid. Drain pump (72) pumps liquid from basin drain (62) to a utility drain (74). A level sensor (76) monitors the flow of liquid from pump (72) to utility drain (74). Pumps (70, 72) can be simultaneously operated such that liquid is sprayed into basin (14*a*) while basin (14*a*) is being drained, to encourage the flow of residue out of basin (14*a*) and off of endoscope (200). Of course, a single pump and a valve assembly could replace dual pumps (70, 72).

An inline heater (80), with temperature sensors (82), upstream of recirculation pump (70), heats the liquid to optimum temperatures for cleaning and/or disinfection. A pressure switch or sensor (84) measures pressure downstream of circulation pump (70). In some variations, a flow sensor is used instead of pressure sensor (84), to measure fluid flow downstream of circulation pump (70). Detergent solution (86) is metered into the flow downstream of circulation pump (70) via a metering pump (88). A float switch (90) indicates the level of detergent (86) available. Disinfectant (92) is metered into the flow upstream of circulation pump (70) via a metering pump (94). To more accurately meter disinfectant (92), a dispensing pump (94) fills a metering pre-chamber (96) under control of a fluid level switch (98) and control system (20). By way of example only, disinfection solution (92) may comprise CIDEX© Activated Glutaraldehyde Solution by Advanced Sterilization Products of Irvine, Calif. By way of further example only, disinfection solution (92) may comprise ortho-phthalaldehyde (OPA). By way of further example only, disinfection solution (92) may comprise peracetic acid (PAA).

Some endoscopes (200) include a flexible outer housing or sheath surrounding the individual tubular members and the like that form the interior channels and other parts of endoscope (200). This housing defines a closed interior space, which is isolated from patient tissues and fluids during medical procedures. It may be important that the sheath be maintained intact, without cuts or other holes that would allow contamination of the interior space beneath the sheath. Therefore, reprocessing system (2) of the present example includes means for testing the integrity of such a sheath. In particular, an air pump (e.g., pump (38) or another pump (110)) pressurizes the interior space defined by the sheath of endoscope (200) through a conduit (112) and a valve (S5). In the present example, a HEPA or other microbe-removing filter (113) removes microbes from the pressurizing air. A pressure regulator (114) prevents accidental over pressurization of the sheath. Upon full pressurization, valve (S5) is closed and a pressure sensor (116)

looks for a drop in pressure in conduit (112), which would indicate the escape of air through the sheath of endoscope (200). A valve (S6) selectively vents conduit (112) and the sheath of endoscope (200) through an optional filter (118) when the testing procedure is complete. An air buffer (120) smoothes out pulsation of pressure from air pump (110).

In the present example, each station (10, 12) also contains a drip basin (130) and spill sensor (132) to alert the operator to potential leaks.

An alcohol supply (134), controlled by a valve (S3), can supply alcohol to channel pumps (32) after rinsing steps, to assist in removing water from channels (210, 212, 213, 214, 217, 218) of endoscope (200).

Flow rates in supply lines (30) can be monitored via channel pumps (32) and pressure sensors (42). If one of pressure sensors (42) detects too high a pressure, the associated pump (32) is deactivated. The flow rate of pump (32) and its activated duration time provide a reasonable indication of the flow rate in an associated line (30). These flow rates are monitored during the process to check for blockages in any of the channels of endoscope (200). Alternatively, the decay in the pressure from the time pump (32) cycles off can also be used to estimate the flow rate, with faster decay rates being associated with higher flow rates.

A more accurate measurement of flow rate in an individual channel may be desirable to detect more subtle blockages. To that end, a metering tube (136) having a plurality of level indicating sensors (138) fluidly connects to the inputs of channel pumps (32). In some versions, a reference connection is provided at a low point in metering tube (136) and a plurality of sensors (138) are arranged vertically above the reference connection. By passing a current from the reference point through the fluid to sensors (138), it can be determined which sensors (138) are immersed and therefore determine the level within metering tube (136). In addition or in the alternative, any other suitable components and techniques may be used to sense fluid levels. By shutting valve (S1) and opening a vent valve (S7), channel pumps (32) draw exclusively from metering tube (136). The amount of fluid being drawn can be very accurately determined based upon sensors (138). By running each channel pump (32) in isolation, the flow therethrough can be accurately determined based upon the time and the volume of fluid emptied from metering tube (136).

In addition to the input and output devices described above, all of the electrical and electromechanical devices shown are operatively connected to and controlled by control system (20). Specifically, and without limitation, switches and sensors (42, 59, 76, 84, 90, 98, 114, 116, 132 136) provide input (I) to microcontroller (28), which controls the cleaning and/or disinfection cycles and other machine operations in accordance therewith. For example, microcontroller (28) includes outputs (O) that are operatively connected to pumps (32, 38, 70, 72, 88, 94, 100, 110), valves (S1, S2, S3, S5, S6, S7), and heater (80) to control these devices for effective cleaning and/or disinfection cycles and other operations.

Figure 3:
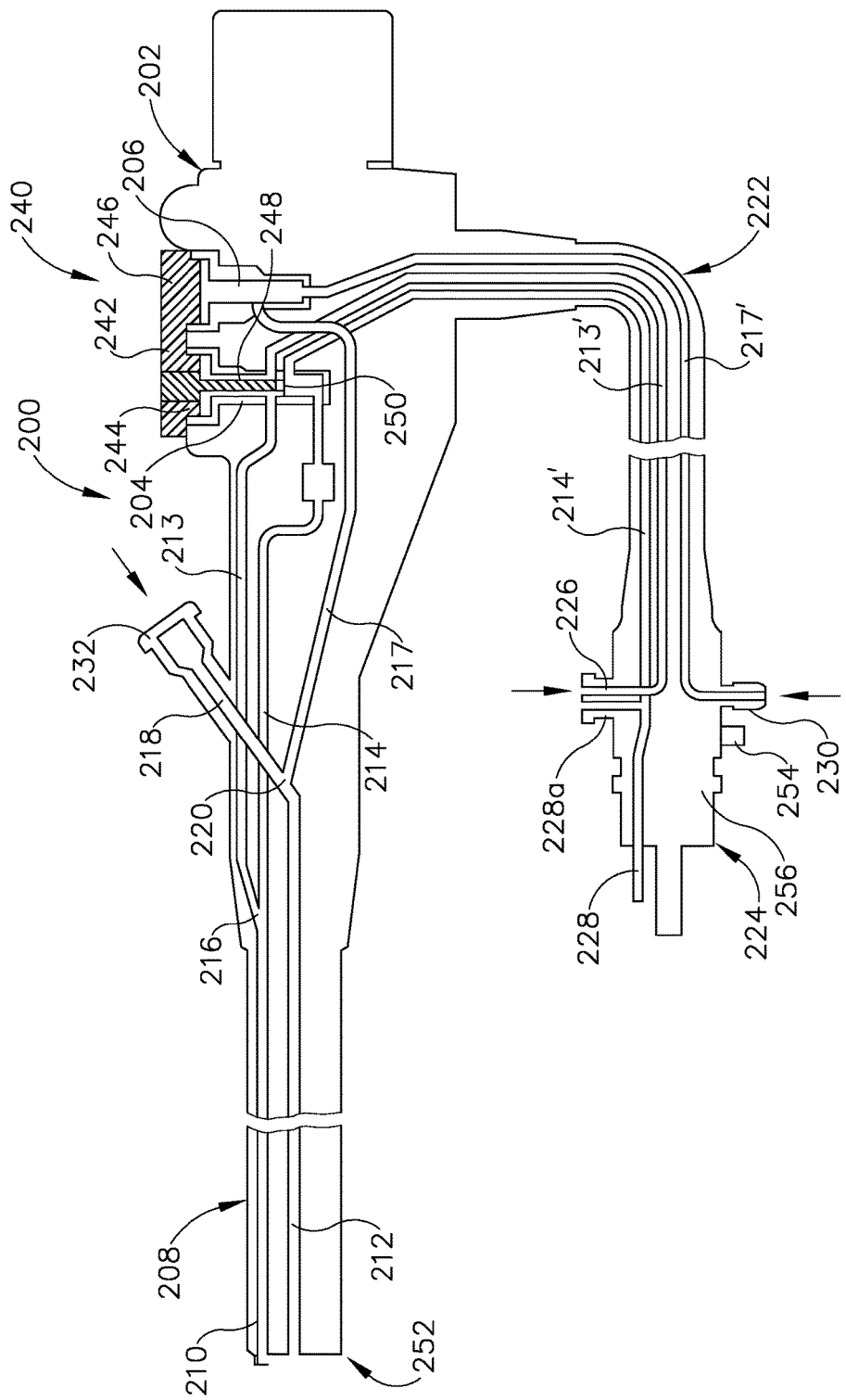
FIG. 3 depicts a cross-sectional side view of proximal and distal portions of an endoscope that may be decontaminated using the reprocessing system of FIG. 1.

As shown in FIG. 3, endoscope (200) has a head part (202). Head part (202) includes openings (204, 206) formed therein. During normal use of endoscope (200), an air/water valve (not shown) and a suction valve (not shown) are arranged in openings (204, 206). A flexible insertion tube (208) is attached to head part (202). A combined air/water channel (210) and a combined suction/biopsy channel (212) are accommodated in insertion tube (208). A separate air channel (213) and water channel (214) are also arranged in head part (202) and merge into air/water channel (210) at the location of a joining point (216). It will be appreciated that the term "joining point" as used herein refers to an intersecting junction rather than being limited to a geometrical point and, the terms may be used interchangeably. Furthermore, a separate suction channel (217) and biopsy channel (218) are accommodated in head part (202) and merge into suction/biopsy channel (212) at the location of a joining point (220).

In head part (202), air channel (213) and water channel (214) open into opening (204) for the air/water valve (not shown). Suction channel (217) opens into opening (206) for the suction valve (not shown). Furthermore, a flexible feed hose (222) connects to head part (202) and accommodates channels (213', 214', 217'), which are connected to air channel (213), water channel (214), and suction channel (217) via respective openings (204, 206). In practice, feed hose (222) may also be referred to as the light-conductor casing. The mutually connecting air channels (213, 213') will collectively be referred to below as air channel (213). The mutually connecting water channels (214, 214') will collectively be referred to below as water channel (214). The mutually connecting suction channels (217, 217') will collectively be referred to below as suction channel (217). A connection (226) for air channel (213), connections (228, 228a) for water channel (214), and a connection (230) for suction channel (217) are arranged on the end section (224) (also referred to as the light conductor connector) of flexible hose (222). When the connection (226) is in use, connection (228a) is closed off. A connection (232) for biopsy channel (218) is arranged on head part (202).

A channel separator (240) is shown inserted into openings (204, 206). Channel separator (240) comprises a body (242) and plug members (244, 246), which occlude respective openings (204, 206). A coaxial insert (248) on plug member (244) extends inwardly of opening (204) and terminates in an annular flange (250), which occludes a portion of opening (204) to separate channel (213) from channel (214). By connecting lines (30) to openings (226, 228, 228a, 230, 232), liquid for cleaning and disinfection can be flowed through endoscope channels (213, 214, 217, 218) and out of a distal tip (252) of endoscope (200) via channels (210, 212). Channel separator (240) ensures that such liquid flows all the way through endoscope (200) without leaking out of openings (204, 206); and isolates channels (213, 214) from each other so that each channel (213, 214) has its own independent flow path. One of skill in the art will appreciate that various endoscopes having differing arrangements of channels and openings may require modifications to channel separator (240) to accommodate such differences while occluding ports in head (202) and keeping channels separated from each other so that each channel can be flushed independently of the other channels. Otherwise, a blockage in one channel might merely redirect flow to a connected unblocked channel.

A leakage port (254) on end section (224) leads into an interior portion (256) of endoscope (200) and is used to check for the physical integrity thereof, namely to ensure that no leakage has formed between any of the channels and the interior (256) or from the exterior to the interior (256).

II. Exemplary Medical Device Reprocessing Method

In an exemplary use of reprocessing system (2) as shown in FIGS. 1-3, an operator may start by actuating a foot pedal (not shown) to open basin lid (16a). Each lid (16a, 16b) may have its own foot pedal. In some versions, once pressure is removed from the foot pedal, the motion of lid (16a, 16b) stops. With lid (16a) open, the operator inserts insertion tube (208) of endoscope (200) into helical circulation tube (64).

End section (224) and head section (202) of endoscope (200) are situated within basin (14a), with feed hose (222) coiled within basin (14a) with as wide a diameter as possible. Next, flush lines (30) are attached to respective endoscope openings (226, 228, 228a, 230, 232). Air line (112) is also connected to a leakage port (254), which may also be referred to herein as a connector. In some versions, flush lines (30) are color coded, and guide located on station (10) provides a reference for the color-coded connections.

Depending on the customer-selectable configuration, control system (20) may prompt the operator to enter a user code, patient ID, endoscope code, and/or specialist code. This information may be entered manually (e.g., through touch screen (22)), automatically (e.g., by using an attached barcode wand), or in any other suitable fashion. With the information entered (if required), the operator may then close lid (16a). In some versions, closing lid (16a) requires the operator to press a hardware button and a touch-screen (22) button simultaneously to provide a fail-safe mechanism for preventing the operator's hands from being caught or pinched by the closing basin lid (16a). If either the hardware button or software button is released while lid (16a) is in the process of closing, the motion of lid (16a) stops.

Once lid (16a) is closed, the operator presses a button on touch-screen (22) to begin the washing/disinfection process. At the start of the washing/disinfection process, air pump (38) is activated and pressure within the body of endoscope (200) is monitored. When pressure reaches a predetermined level (e.g., 250 mbar), pump (38) is deactivated, and the pressure is allowed to stabilize for a certain stabilization period (e.g., 6 seconds). If pressure has not reached a certain pressure (e.g., 250 mbar) in a certain time period (e.g., 45 seconds), the program is stopped and the operator is notified of a leak. If pressure drops below a threshold (e.g., less than 100 mbar) during the stabilization period, the program is stopped and the operator is notified of the condition. Once the pressure has stabilized, the pressure drop is monitored over the course of a certain duration (e.g., 60 seconds). If pressure drop is faster than a predetermined rate (e.g., more than 10 mbar within 60 seconds), the program is stopped and the operator is notified of the condition. If the pressure drop is slower than a predetermined rate (e.g., less than 10 mbar in 60 seconds), reprocessing system (2) continues with the next step. A slight positive pressure is held within the body of endoscope (200) during the rest of the process to prevent fluids from leaking in.

A second leak test checks the adequacy of connection to the various ports (226, 228, 228a, 230, 232) and the proper placement of channel separator (240). A quantity of water is admitted to basin (14a) so as to submerge the distal end of endoscope (200) in helical tube (64). Valve (S1) is closed and valve (S7) opened; and pumps (32) are run in reverse to draw a vacuum and to ultimately draw liquid into endoscope channels (210, 212). Pressure sensors (42) are monitored to make sure that the pressure in any one channel (210, 212) does not drop and/or raise by more than a predetermined amount in a given time frame. If it does, it likely indicates that one of the connections was not made correctly and air is leaking into channel (210, 212). In any event, in the presence of an unacceptable pressure drop, control system (20) will cancel the cycle and indicate a likely faulty connection, preferably with an indication of which channel (210, 212) failed.

In the event that the leak tests are passed, reprocessing system (2) continues with a pre-rinse cycle. The purpose of this step is to flush water through channels (210, 212, 213, 214, 217, 218) to remove waste material prior to washing and disinfecting endoscope (200). To initiate the pre-rinse cycle, basin (14a) is filled with filtered water and the water level is detected by pressure sensor (59) below basin (14a). The water is pumped via pumps (32) through the interior of channels (210, 212, 213, 214, 217, 218), directly to drain (74). This water is not recirculated around the exterior surfaces of endoscope (200) during this stage. As the water is being pumped through channels (210, 212, 213, 214, 217, 218), drain pump (72) is activated to ensure that basin (14a) is also emptied. Drain pump (72) will be turned off when drain switch (76) detects that the drain process is complete. During the draining process, sterile air is blown via air pump (38) through all endoscope channels (210, 212, 213, 214, 217, 218) simultaneously, to minimize potential carryover.

Once the pre-rinse cycle is complete, reprocessing system (2) continues with a wash cycle. To begin the wash cycle, basin (14a) is filled with warm water (e.g., approximately 35° C.). Water temperature is controlled by controlling the mix of heated and unheated water. The water level is detected by pressure sensor (59). Reprocessing system (2) then adds enzymatic detergent to the water circulating in reprocessing system (2) by means of peristaltic metering pump (88). The volume is controlled by controlling the delivery time, pump speed, and inner diameter of the tubing of pump (88). Detergent solution (86) is actively pumped throughout the internal endoscope channels (210, 212, 213, 214, 217, 218) and over the outer surface of endoscope (200) for a predetermined time period (e.g., from one to five minutes, or more particularly about three minutes), by channel pumps (32) and external circulation pump (70). Inline heater (80) keeps the temperature at a predetermined temperature (e.g., approximately about 35° C.).

After detergent solution (86) has been circulating for a certain period of time (e.g., a couple of minutes), the flow rate through channels (210, 212, 213, 214, 217, 218) is measured. If the flow rate through any channel (210, 212, 213, 214, 217, 218) is less than a predetermined rate for that channel (210, 212, 213, 214, 217, 218), the channel (210, 212, 213, 214, 217, 218) is identified as blocked, the program is stopped, and the operator is notified of the condition. Peristaltic pumps (32) are run at their predetermined flow rates and cycle off in the presence of unacceptably high pressure readings at the associated pressure sensor (42). If a channel (210, 212, 213, 214, 217, 218) is blocked, the predetermined flow rate will trigger pressure sensor (42), indicating the inability to adequately pass this flow rate. As pumps (32) are peristaltic in the present example, their operating flow rate combined with the percentage of time they are cycled off due to pressure will provide the actual flow rate. The flow rate can also be estimated based upon the decay of the pressure from the time pump (32) cycles off.

At the end of the wash cycle, drain pump (72) is activated to remove detergent solution (86) from basin (14a) and channels (210, 212, 213, 214, 217, 218). Drain pump (72) turns off when drain level sensor (76) indicates that drainage is complete. During the drain process, sterile air is blown through all channels (210, 212, 213, 214, 217, 218) of endoscope (200) simultaneously to minimize potential carryover.

After the wash cycle is complete, reprocessing system (2) begins a rinse cycle. To initiate this rinse cycle, basin (14a) is again filled with warm water (e.g., at approximately 35° C.). Water temperature is controlled by controlling the mix of heated and unheated water. The water level is detected by pressure sensor (59). The rinse water is circulated within channels (210, 212, 213, 214, 217, 218) of endoscope (200) via channel pumps (32); and over the exterior of endoscope (200) via circulation pump (70) and sprinkler arm (60) for a certain period of time (e.g., one minute). As rinse water is pumped through channels (210, 212, 213, 214, 217, 218), the flow rate through channels (210, 212, 213, 214, 217, 218) is measured and if it falls below the predetermined rate for any given channel (210, 212, 213, 214, 217, 218), that channel (210, 212, 213, 214, 217, 218) is identified as blocked, the program is stopped, and the operator is notified of the condition.

At the end of the rinse cycle, drain pump (72) is activated to remove the rinse water from basin (14a) and channels (210, 212, 213, 214, 217, 218). Drain pump (72) turns off when drain level sensor (76) indicates that drainage is complete. During the drain process, sterile air is blown through all channels (210, 212, 213, 214, 217, 218) of endoscope (200) simultaneously to minimize potential carryover. In some versions, the above-described rinsing and draining cycles are repeated at least once again, to ensure maximum rinsing of detergent solution (86) from the surfaces of endoscope (200) and basin (14a).

After reprocessing system (2) has completed the desired number of rinsing and drying cycles, reprocessing system (2) proceeds to a disinfection cycle. To initiate the disinfection cycle, basin (14a) is filled with very warm water (e.g., at approximately 53° C.). Water temperature is controlled by controlling the mix of heated and unheated water. The water level is detected by pressure sensor (59). During the filling process, channel pumps (32) are off in order to ensure that the disinfectant solution (92) in basin (14a) is at the in-use concentration prior to circulating through channels (210, 212, 213, 214, 217, 218) of endoscope (200).

Next, a measured volume of disinfection solution (92) is drawn from disinfectant metering pre-chamber (96) and delivered into the water in basin (14a) via metering pump (100). The volume of disinfection solution (92) is controlled by the positioning of fill level switch (98) relative to the bottom of metering pre-chamber (96). Metering pre-chamber (96) is filled until fill level switch (98) detects liquid. Disinfection solution (92) is drawn from metering pre-chamber (96) until the level of disinfection solution (92) in metering pre-chamber (96) is just below the tip of metering pre-chamber (96). After the necessary volume is dispensed, metering pre-chamber (96) is refilled from the bottle of disinfection solution (92). Disinfection solution (92) is not added until basin (14a) is filled, so that in case of a water supply problem, concentrated disinfectant is not left on endoscope (200) with no water to rinse it. While disinfection solution (92) is being added, channel pumps (32) are off in order to ensure that disinfection solution (92) in basin (14a) is at the desired in-use concentration prior to circulating through channels (210, 212, 213, 214, 217, 218) of endoscope (200).

The in-use disinfectant solution (92) is actively pumped throughout internal channels (210, 212, 213, 214, 217, 218) by pumps (32) and over the outer surface of endoscope (200) by circulation pump (70). This may be done for any suitable duration (e.g., at least 5 minutes). The temperature of the disinfection solution (92) may be controlled by in-line heater (80) to stay at a consistent temperature (e.g., about 52.5° C.). During the disinfection process, flow through each channel (210, 212, 213, 214, 217, 218) of endoscope (200) is verified by timing the delivering a measured quantity of solution through channel (210, 212, 213, 214, 217, 218). Valve (S1) is closed, and valve (S7) opened, and in turn each channel pump (32) delivers a predetermined volume to its associated channel (210, 212, 213, 214, 217, 218) from metering tube (136). This volume and the time it takes to deliver the volume, provides a very accurate flow rate through the channel (210, 212, 213, 214, 217, 218). Anomalies in the flow rate from what is expected for a channel (210, 212, 213, 214, 217, 218) of that diameter and length are flagged by control system (20) and the process stopped. As in-use disinfection solution (92) is pumped through channels (210, 212, 213, 214, 217, 218), the flow rate through channels (210, 212, 213, 214, 217, 218) is also measured as described above.

At the end of the disinfection cycle, drain pump (72) is activated to remove disinfectant solution from basin (14a) and channels (210, 212, 213, 214, 217, 218). During the draining process, sterile air is blown through all channels (210, 212, 213, 214, 217, 218) of endoscope (200) simultaneously to minimize potential carryover.

After disinfection solution (92) has been drained from basin (14a), reprocessing system (2) begins a final rinse cycle. To initiate this cycle, basin (14a) is filled with sterile warm water (e.g., at approximately 45° C.) that has been passed through a filter (e.g., a 0.2 μm filter). The rinse water is circulated within channels (210, 212, 213, 214, 217, 218) by pumps (32); and over the exterior of endoscope (200) via circulation pump (70) and sprinkler arm 60) for a suitable duration (e.g., 1 minute). As rinse water is pumped through channels (210, 212, 213, 214, 217, 218), the flow rate through channels (210, 212, 213, 214, 217, 218) is measured as described above. Drain pump (72) is activated to remove the rinse water from basin (14a) and channels (210, 212, 213, 214, 217, 218). During the draining process, sterile air is blown through all channels (210, 212, 213, 214, 217, 218) of endoscope (200) simultaneously to minimize potential carryover. In some versions, the above-described rinsing and draining cycles are repeated at least two more times, to ensure maximum rinsing of disinfection solution (92) residuals from the surfaces of endoscope (200) and basin (14a).

After the final rinse cycle is complete, reprocessing system (2) begins a final leak test. In particular, reprocessing system (2) pressurizes the body of endoscope (200) and measures the leak rate as described above. If the final leak test is successful, reprocessing system (2) indicates the successful completion of the cycles via touch-screen (22). From the time of program completion to the time at which lid (16a) is opened, pressure within the body of endoscope (200) is normalized to atmospheric pressure by opening vent valve (S5) at a predetermined rate (e.g., valve (S5) opened for 10 seconds every minute).

Depending on customer-selected configuration, reprocessing system (2) may prevent lid (16a) from being opened until a valid user identification code is entered. Information about the completed program, including the user ID, endoscope ID, specialist ID, and patient ID are stored along with the sensor data obtained throughout the program. If a printer is connected to reprocessing system (2), and if requested by the operator, a record of the disinfection program will be printed. Once a valid user identification code has been entered, lid (16a) may be opened (e.g., using the foot pedal as described above). Endoscope (200) is then disconnected from flush lines (30) and removed from basin (14a). Lid (16a) can then be closed using both the hardware and software buttons as described above.

III. Exemplary Flush Conduits with Various Discharge Flow Rates

In some instances, it may be desirable to reduce the number of pumps (32) within reprocessing system (2) in order to reduce the overall cost and, in some instances, complexity of reprocessing system (2), while still maintaining performance for each of the above referenced cycles. For example, reducing the number of pumps (32) may not only reduce the cost of manufacturing reprocessing system (2), but also reduce expected pump maintenance costs associated with continued use of reprocessing system (2). One such exemplary reprocessing system (310) described below with respect to FIG. 4 includes one such pump (312) fluidly connected to flush lines (30). One single pump (312) thus simultaneously provides fluid to each flush line (30), rather than separate pumps (32) for each respective flush line (30).

In order to achieve the above referenced flow rates through flush lines (30), which may vary in some predetermined differences to accommodate various medical devices, reprocessing system (310) further includes additional valves, such as flush valves (314, 316, 318, 320) that are configured to balance fluid flow relative to a predetermined supply flow rate delivered via pump (312). Flush valves (314, 316, 318, 320) thus distribute flow through each respective flush line (30) to achieve similar and/or different flow rates according to some desirable, predetermined distribution of fluid flow similar to the plurality of pumps (32) discussed above. It will be appreciated that any desirable combination of predetermined flow rates may be used in any such system, such as flush lines (30). Thus, the invention described herein is not intended to be unnecessarily limited to the particular pump (312) and valve arrangement, such as flush valves (314, 316, 318, 320). Alternative embodiments of reprocessing system (310', 410, 510, 610) discussed herein also include such valve flow rate control. It will be appreciated that various aspects of valve flow rate control may be used with respect to any of reprocessing systems (2, 310, 310', 410, 510, 610) and in any combination as described herein.

Figure 4:
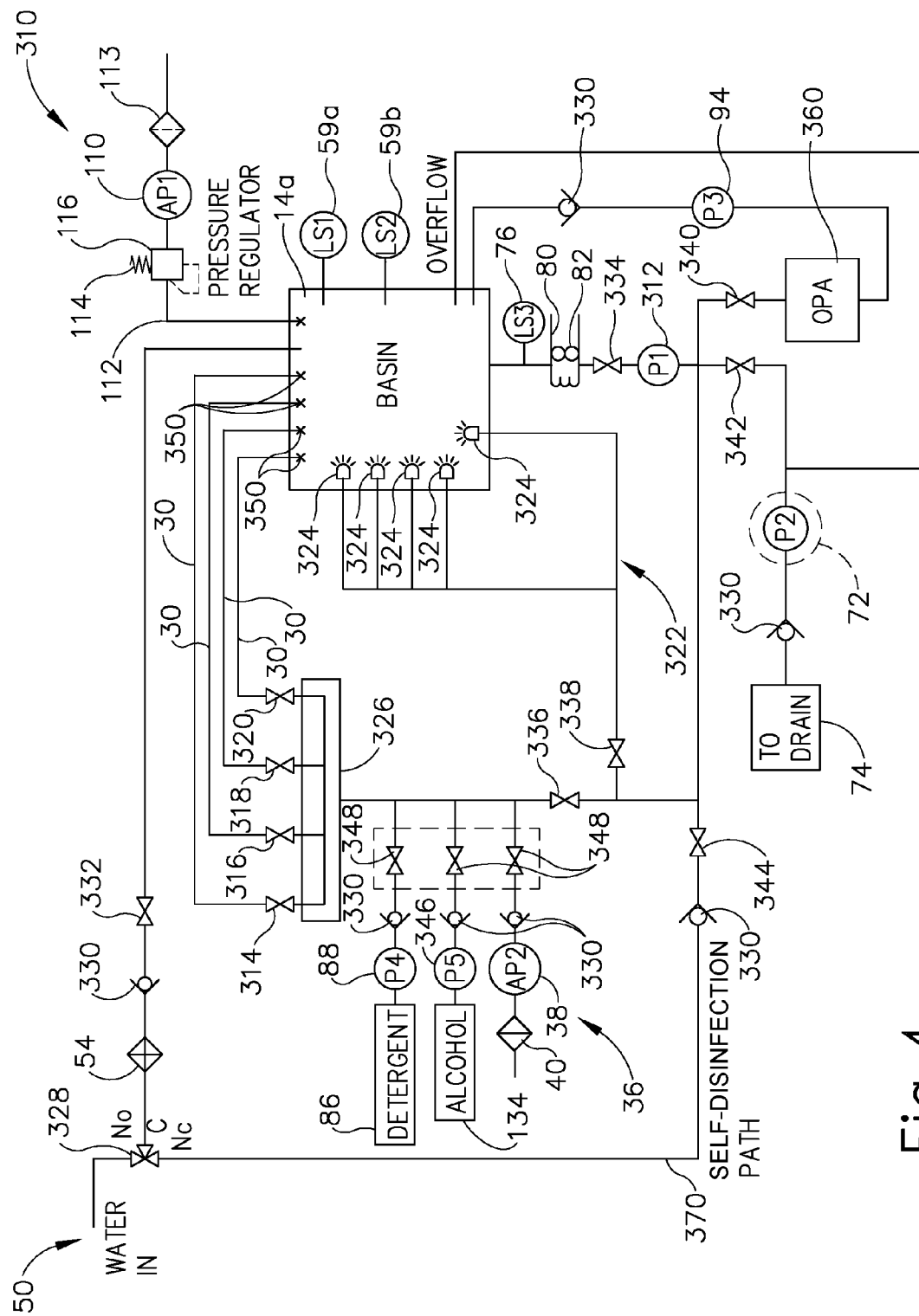
FIG. 4 depicts a schematic diagram of a second exemplary reprocessing system.

FIG. 4 shows a schematic of a second exemplary reprocessing system (310) that may be incorporated into stations (10, 12) (see FIG. 1) with basins (14a, 14b). Basin (14a) shown in FIG. 4 thus receives water from water source (50) and discharges all water therefrom via drain (74), as discussed above. Exemplary basin (14a) includes a plurality of flush lines (30) extending therein and a nozzle assembly (322) having a plurality of nozzles (324). Each flush line (30) and nozzle (324) is configured to direct the water and/or any additive solution, which may be generally referred to as the fluid, toward endoscope (200) (see FIG. 3) within basin (14a) for reprocessing. As discussed above, flush lines (30) are configured to discharge the fluid into respective channels (210, 212, 217, 218) (see FIG. 3), at respective predetermined conduit flow rates particularly configured for each respective channel (210, 212, 217, 218) (see FIG. 3). To this end, primary pump (312) pumps a predetermined supply flow rate of the fluid collectively to flush lines (30) via a common manifold (326) that is fluidly coupled therebetween.

A plurality of flush valves (314, 316, 318, 320) are positioned respectively in each flush line (30) and are collectively configured to balance fluid flow from primary pump (312) such that each flush line (30) discharges fluid therefrom at respective predetermined conduit flow rates. In some versions, flush lines (30) deliver four different respective predetermined conduit flow rates of fluid to channels (210, 212, 217, 218) (see FIG. 3). In some other versions, one or more of the respective predetermined conduit flow rates are approximately equivalent to accommodate an alternative medical device. In any case, any number of flush lines (30) configured to deliver fluid at any predetermined conduit flow rates may be used to accommodate one or more types of medical devices.

Water source (50) delivers the water to a three-way introduction valve (328), which directs the water through filter (54), check valve (330), and two-way valve (332) into basin (14a). Similar to reprocessing system (2) (see FIG. 2), the water may be collected to a desirable amount as detected by level sensors (59a, 59b, 76). The water drains from basin (14a) and may pass through heater (80) and two-way valve (334) to reach primary pump (312) for distribution toward flush lines (30) and nozzle assembly (322). More particularly a collection of two-way valves (336, 338, 340, 342, 344) are fluidly connected downstream of primary pump (312) to either allow or inhibit fluid flow therethrough for various cycles as discussed herein. For example, flush valve (336) and nozzle valve (338) are configured to control flow respectively toward flush lines (30) and nozzle assembly (322).

In addition, disinfectant valve (340), drain valve (342), and return valve (344) are respectively configured to provide disinfection of endoscope (200) (see FIG. 1), drainage from reprocessing system (310), and self-disinfection of reprocessing system (310). Specifically, disinfection and self-disinfection will be discussed below in additional detail. In the present example, disinfection valve (340), drain valve (342), and return valve (344) are presumed fully closed so as to direct the entirety of the predetermined supply flow of the fluid through the opened flush and nozzle valves (336, 338). However, the collection of valves (336, 338, 340, 342, 344) may be fully opened, partially opened, and/or fully closed so as to direct the fluid in any one of a plurality of desirable ratios to complete the cycles of reprocessing. The invention is thus not intended to be limited specifically to the combination of open and/or closed valves as described herein.

Downstream of flush valve (336), additive storages, such as detergent and alcohol storage (86, 134), and detergent metering pump (88), an alcohol metering pump (346), and a gas pump (38) fluidly connect to be received with or in place of water flowing toward flush lines (30). A series of optional two-way valves (348) may be fluidly connected downstream of pumps (88, 346, 38) for additional flow control of various additives. In any case, the fluid, such as water, is received within manifold (326) at the predetermined supply flow rate. As shown in exemplary reprocessing system (310) of FIG. 4, each of the four flush lines (30) fluidly connects to manifold (326) and extends into basin (14a) for connection with channels (210, 212, 217, 218) (see FIG. 3) of endoscope (200). More particularly, each flush line (30) includes a coupling port (350) within basin (14a) that is configured to fluidly seal against endoscope (200) for fluidly coupling channels (210, 212, 217, 218) (see FIG. 3) with respective flush lines (30).

As briefly discussed above, each flush line (30) includes its respective flush valve (314, 316, 318, 320) configured to balance fluid flows along flush lines (30) according to the predetermined conduit flow rates. In some versions, flush valves (314, 316, 318, 320) are in the form of orifice valves that are sized relative to each to each other to create predetermined restriction on the fluid entering manifold (326) according to the predetermined supply flow rate. As the pressure within the manifold (326) distributes equally through flush lines (30), predetermined conduit flow rates of fluid flow through each respective flush valve (314, 316, 318, 320) and discharge from coupling ports (350). Alternatively, flush valves (314, 316, 318, 320) may each comprise a variable valve configured to provide a discrete, predetermined flow rate so that the operator may adjust various flow rates to accommodate differing medical devices in reprocessing system (310).

Furthermore, nozzle valve (338) also receives the fluid, such as water, from primary pump (312) and directs the fluid toward nozzle assembly (322). Each nozzle (324) is generally identical in the present example and configured to discharge fluid onto the exterior of endoscope (200) (see FIG. 3) within basin (14a) at approximately equivalent predetermined nozzle flow rates. To this end, nozzle valve (338) is configured to further balance the predetermined supply flow rate of fluid with flush valves (314, 316, 318, 320) such that each nozzle (324) and fluid line (30) discharges fluid therefrom according to its predetermined conduit flow rate and predetermined nozzle flow rate, respectively. Similar to flush valves (314, 316, 318, 320), nozzle valve (338) may also be a variable valve configured to set to a discrete, predetermined flow rate so that the operator may adjust various flow rates to accommodate differing medical devices in reprocessing system (310). Alternatively, nozzle valve (338) in an open position may provide negligible resistance such that the various predetermined flow rates are balanced simply by restriction in each respective nozzle (324).

In use, reprocessing system (310) receives water from water supply (50) into basin (14a). Alternatively, basin (14a) may receive one of the additives alone or in combination with the water. In any case, the fluid collected within basin (14a) is received within primary pump (312) and pumped therefrom at the predetermined supply flow rate. The collection of valves (338, 340, 342, 344) are generally configured to direct the fluid at the predetermined supply flow rate toward manifold (326) and nozzle assembly (322). The fluid flowing toward manifold (326) may also receive one of the additives, such as detergent, as discussed above in additional detail.

A predetermined portion of the fluid flows into manifold (326), while a remaining predetermined portion of the fluid flows through nozzle valve (338). Flush valves (336) and nozzle valve (338) generate predetermined restriction in each respective flush line (30) in order to direct fluid flow along each flush line (30) with at least two different respective predetermined conduit flow rates. Such predetermined restriction and restriction results in flush valves (336) and nozzle valve (338) apportioning the fluid flow therethrough according to the various predetermined flow rates. For example, flush valves (336) and nozzle valve (338) may be configured to direct fluid along four flush lines (30) with four different respective predetermined conduit flow rates. Once balanced accordingly, the fluid discharges from each coupling port (350) and into respective channels (210, 212, 217, 218) (see FIG. 3) with the predetermined conduit flow rates for reprocessing endoscope (200) (see FIG. 3). It will be appreciated that generating such predetermined flow rates via valves (336, 338) may be used in any cycle of reprocessing described herein and is not intended to limit the invention to any specific reprocessing cycle.

Reprocessing system (310) of the present example includes only one primary pump (312) supplying the predetermined supply flow rate of fluid to each flush line (30) and nozzle (324). However, it will be appreciated that any number of pumps may be used in combination, such as in series or parallel, to direct fluid as discussed above. It will therefore be appreciated that the invention is not intended to unnecessarily be limited to only one primary pump (312).

IV. Exemplary Medical Device Reprocessing Apparatus and Reusable Disinfectant

In some instances, it may be desirable to collect and reuse disinfectant one or more times rather than drain and dispose of the disinfectant after a single use. For example, reusing disinfectant uses less total disinfectant over the useful life of reprocessing system (2) and may thus decrease the overall cost of operation. In addition, concentrated disinfectant, such as the disinfectant provided from disinfectant storage (92), may have a damaging effect on or more portions of reprocessing system (2) until mixed with water as a disinfectant solution in the desired concentrations. Storing and reusing the disinfectant solution thus reduces the presence of concentrated disinfectant and may thus increase the useful life of reprocessing system (2).

One such exemplary reprocessing system (310) has a disinfectant storage reservoir (360) from which to pump the disinfectant to basin (14a) and collect the disinfectant after completion of the disinfection cycle. Alternative versions of reprocessing system (310', 410, 510, 610) discussed herein also include exemplary disinfection storage reservoir (360). It will be appreciated that various aspects of reusing disinfectant may be used with respect to any of reprocessing systems (2, 310, 310', 410, 510, 610) and in any combination as described herein.

Second exemplary reprocessing system (310) includes primary pump (312), which receives the fluid, such as the water and/or disinfectant, and pumps the fluid toward the collection of valves (336, 338, 340, 342, 344) as discussed above with respect to various cycles. More particularly, disinfection valve (340) is configured to transition between a circulation state and a collection state during the disinfection cycle. With disinfection valve (340) in the circulation state, the collection of valves (336, 338, 340, 342, 344) is configured to return disinfectant toward flush lines (30) and nozzle assembly (322) for continued circulation during reprocessing. At the conclusion of the disinfection cycle, disinfection valve (340) transitions from the circulation state to the collection state and, in conjunction with the remaining collection of valves (336, 338, 342, 344), directs the disinfectant into disinfectant storage reservoir (360) for reuse in future disinfection cycles. As used herein, the term "disinfectant" refers to concentrated disinfectant or any solution including disinfectant at any concentration. The term "disinfectant" is thus not intended to unnecessarily limit the invention to a particular solution of disinfectant.

Reprocessing system (310) further includes disinfectant pump (94) in fluid communication between disinfectant storage reservoir (360) and basin (14a). Disinfectant pump (94) thus pumps the disinfectant directly into basin (14a). Check valve (330) is also fluidly connected between basin (14a) and disinfectant pump (94) and configured to inhibit fluid from within basin (14a) from flowing backward toward pump (94). In one example, disinfectant storage reservoir (360) is in the form of a break tank such that primary pump (312) and disinfectant pump (94) are configured to individually and/or simultaneously interact with disinfectant storage reservoir (360). However, it will be appreciated that alternative couplings and other features may be used to fluidly couple any form of disinfectant storage reservoir (360) within reprocessing system (310) for collecting and reusing disinfectant. The invention is thus not intended to be limited to the particular disinfectant storage reservoir (360).

Figure 5:
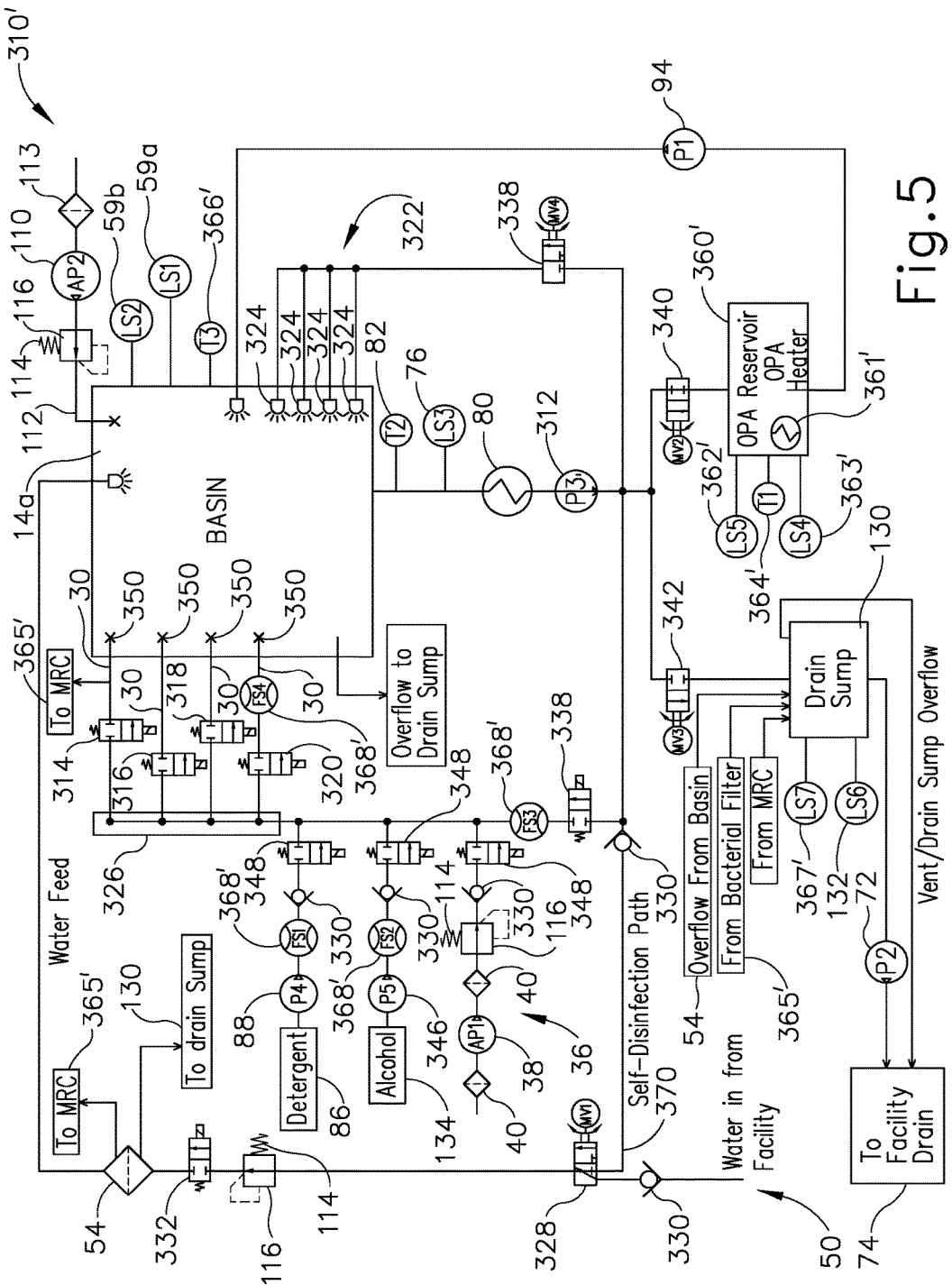
FIG. 5 depicts a schematic diagram of a third exemplary reprocessing system.

A third exemplary reprocessing system (310') has another exemplary disinfectant storage reservoir (360') fluidly connected between disinfectant valve (340) and pump (94) as shown in FIG. 5. Disinfectant storage reservoir (360') is generally similar to disinfectant storage reservoir (360) (see FIG. 4), but also includes additional features for further preparing and maintaining the disinfectant for reprocessing. Specifically, disinfectant storage reservoir (360') includes a disinfectant heater (361') configured to heat the disinfectant for reprocessing. In one example, disinfectant heater (361') is configured to pre-heat the disinfectant in anticipation of use in order to more quickly heat the fluid circulating through reprocessing system (310') for reasons discussed below in additional detail. Alternatively or in addition, disinfectant heater (361') may heat the disinfectant while flowing from disinfectant storage reservoir (360') toward pump (94) for use. In either case, disinfectant heater (361') may be configured to heat the fluid in conjunction with heater (80) for collectively heating the fluid as it flows through reprocessing system (310').

Disinfectant storage reservoir (360') further includes a maximum level sensor (362'), a minimum level sensor (363'), and a temperature sensor (364') for monitoring the disinfectant flowing through and/or contained within disinfectant storage reservoir (360'). Maximum and minimum level sensors (362', 363') are configured to approximate the amount of disinfectant contained within disinfectant storage reservoir (360') and communicate with another system, such as control system (20) (see FIG. 1). For example, maximum and minimum level sensors (362', 363') and control system (20) (see FIG. 1) collectively monitor the amount of disinfectant to be above the maximum level, below the minimum level, or between the maximum and minimum levels, which is generally desired for operation. Temperature sensor (364') also communicates with another system, such as control system (20) (see FIG. 1), to monitor the temperature of the disinfectant.

In order to further monitor the disinfectant, reprocessing system (310') also includes a disinfectant concentration measuring subsystem (365') that is configured to receive the disinfectant from at least one location within reprocessing system (310') for sampling and testing. To this end, disinfectant concentration measuring subsystem (365') of the present example receives the disinfectant samples from filter (54) and from at least one of flush lines (30). Disinfectant concentration measuring subsystem (365') is configured to test samples of disinfectant received from filter (54) and flush line (30) for a concentration of disinfectant present within the fluid flowing therethrough. In the event that the measured concentration of disinfectant is not within a predetermined range of concentration or is below a predetermined minimum concentration, disinfectant concentration measuring subsystem (365') notifies the operator accordingly. Such measurement and notification may be further aided by communication with control system (20) (see FIG. 1) discussed above in greater detail. Upon completion of sampling and testing, the disinfectant drains to drain sump (130) such that disinfectant concentration measuring subsystem (365') is available for further use. In parallel, filter (54) also drains directly to drain sump (130) in the event that fluid is not directed toward disinfectant concentration measuring subsystem (365'). It will be appreciated that various devices and method for measuring disinfectant concentration and notifying the operator may be used as described herein and, as such, the invention is not intended to be unnecessarily limited to any particular disinfectant concentration measuring subsystem. By way of further example only, disinfectant concentration measuring subsystem (365') may be configured and operable in accordance with at least some of the teachings of U.S. patent application Ser. No. 15/157,952, entitled "Apparatus and Method to Measure Concentration of Disinfectant in Medical Device Reprocessing System," filed on May 18, 2016, published as U.S. Pub. No. 2017/0333584 on Nov. 23, 2017, the disclosure of which is incorporated by reference herein.

Additional monitoring is provided in reprocessing system (310') by a basin temperature sensor (366'), a drain sump overflow sensor (367'), and a plurality of flow sensors (368'). Basin temperature sensor (366') is generally configured to measure the temperature of fluid therein, while drain sump overflow sensor (367') is configured to measure an excess of fluid collected within drain sump (130) for alerting the operator. Each flow sensor (368') is configured to measure the volumetric flow rate of fluid flowing therethrough for monitoring the overall circulation of fluid through reprocessing system (310'). Each of temperature sensor (366'), drain sump overflow sensor (367'), and flow sensors (368') may communicate with control system (20) (see FIG. 1) for collective operation with any one or more of the sensors discussed herein for using reprocessing system (310). However, it will be appreciated that alternative devices and methods of monitoring reprocessing system (310') may be used and that the invention described herein is not intended to be unnecessarily limited to reprocessing system (310').

Figure 6:
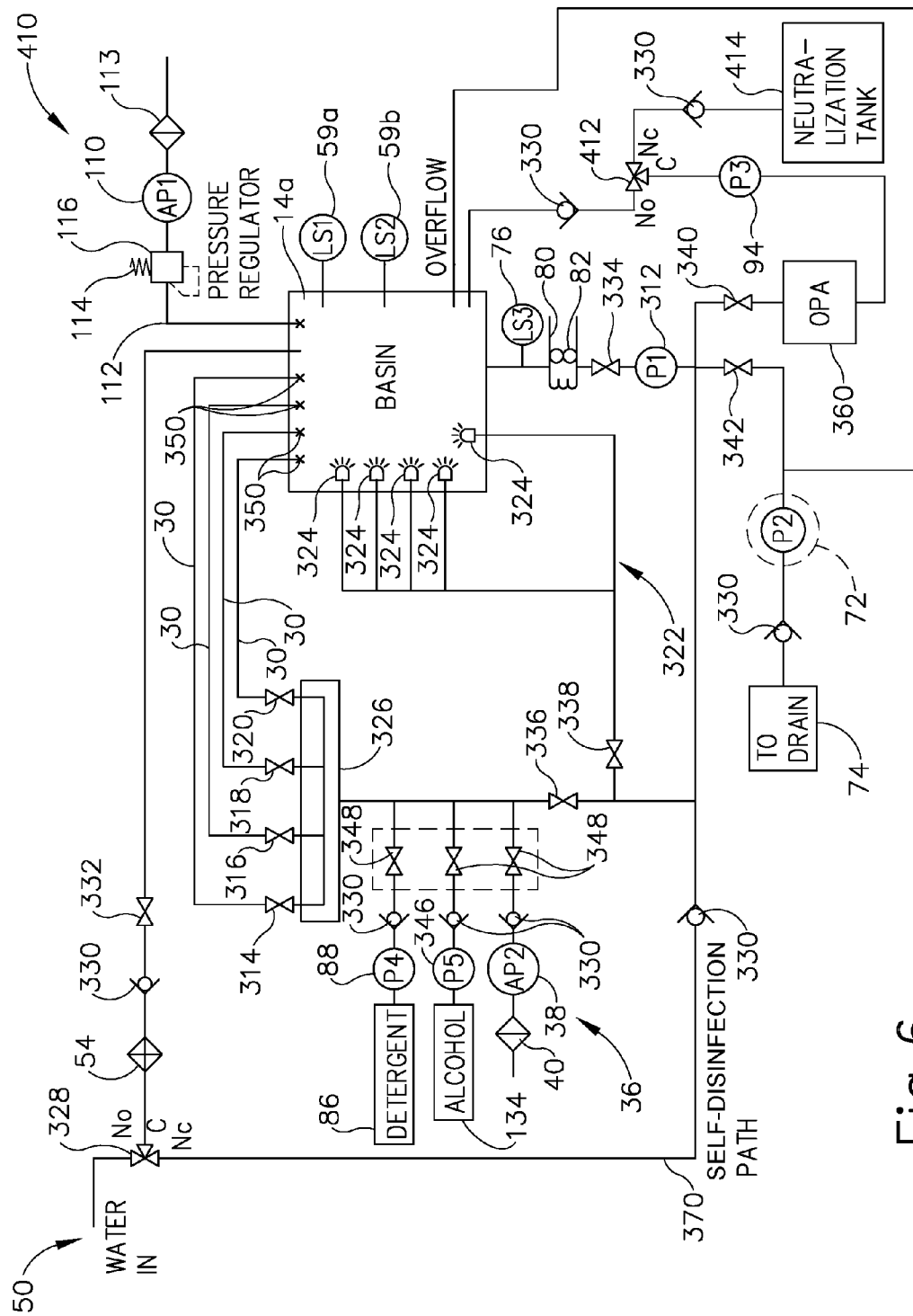
FIG. 6 depicts a schematic diagram of a fourth exemplary reprocessing system.

By way of further example, a fourth exemplary reprocessing system (410) is shown in FIG. 6. Reprocessing system (410) of this example generally includes disinfectant reservoir (360), disinfectant pump (94), and check valve (330) fluidly connected between basin (14a) and disinfectant valve (340). In addition, a three-way neutralization valve (412) is fluidly connected between check valve (330) and disinfectant pump (98) and is in fluid communication with a neutralization tank (414). Neutralization tank (414) is configured to receive the disinfectant and neutralize some or all of its sterilizing properties for disposal as dictated by various rules and regulations. Neutralization tank (414) is also removable from reprocessing system (410) to ease operator access to neutralized disinfectant for proper disposal.

To initiate the disinfection cycle of reprocessing system (310) shown in FIG. 4, disinfectant pump (94) pumps the disinfectant from disinfectant storage reservoir (360) toward basin (14a). The disinfectant contained in disinfectant storage reservoir (360) may be premixed to a desirable concentration or mixed with water in basin (14a) as discussed above with respect to reprocessing system (2) (see FIG. 2). From basin (14a), the disinfectant is circulated through flush lines (30) and nozzle assembly (322) for disinfecting endoscope (200) (see FIG. 3) via primary pump (312). In addition, heater (80) heats the disinfectant for disinfection.

Rather than necessarily disposing of the disinfectant after disinfecting endoscope (200) (see FIG. 3), disinfection valve (340) opens such that primary pump (312) directs the disinfectant into disinfectant storage reservoir (360). Disinfection valve (340) then closes to inhibit other fluids from entering the disinfectant storage reservoir (360) so that other cycles for reprocessing may be completed. The disinfectant is contained in disinfectant storage reservoir (360) and available for reuse in future disinfection cycles. In the event that the disinfectant needs to be replaced, such as due to contamination, dilution of disinfectant below a predetermined concentration, or following a predetermined number of use, the operator manipulates a drain hose (not shown) in fluid communication with drain (74) and directs the drain hose into another container, such as neutralization tank (414) (see FIG. 6), for collection and proper disposal.

In contrast, reprocessing system (410) shown in FIG. 6 generally operates disinfection cycle as discussed above, but, instead, the disinfectant is pumped into neutralization tank (414). More particularly, neutralization valve (412) is configured to transition between a basin state and a neutralization state. In the basin state, neutralization valve (412) directs the disinfectant to basin (14a). In the neutralization state, neutralization valve (412) directs the disinfectant to neutralization tank (414). Disinfectant pump (94) thus pumps the disinfectant from disinfectant storage reservoir (360) and into neutralization tank (414) for neutralization, removal, and proper disposal.

V. Exemplary Medical Device Reprocessing Apparatus with Self-Disinfection Cycle

In some instances, it may be desirable to sterilize reprocessing system (2) with disinfectant and/or heated water for chemical and/or and thermal disinfection to perform a "self-disinfection cycle.". However, in order to fully disinfect reprocessing system (2), fluid (i.e., disinfectant and/or heated water) is preferably flushed through the entire reprocessing system (2) that may have come into contact with endoscope (200) and/or waste material. Even in the event that chemical and/or thermal disinfection provides such thorough contact, reprocessing system (2) may require a relatively significant amount of fluid for self-disinfection, resulting in increased cost of operation. Furthermore, operation of the self-disinfection cycle may include manual manipulation of various valves and conduits to both provide the disinfectant and sufficiently heat the disinfectant for effective chemical and thermal sterilization. Such costs and operator inconvenience may decrease the likelihood of the operator performing the self-disinfection cycle, thus increasing the likelihood that reprocessing system (2) may not be fully sterilized in advance of reprocessing an endoscope (200). It may thus be desirable to provide reprocessing system (2) with one or more features configured to perform convenient chemical and/or thermal disinfection while also reducing the amount of fluid, such as disinfectant and/or heated water, disposed of following completion of the self-disinfection cycle.

As shown in FIGS. 4-6, exemplary reprocessing systems (310, 310', 410) include a return flow path (370) that is configured to guide the fluid, such as disinfectant and/or heated water, from primary pump (312) to introduction valve (328). Reprocessing systems (310, 310', 410) are thus configured to direct the fluid throughout portions thereof that may have contacted endoscope (200) and/or waste material removed from endoscope (200). Reprocessing systems (310, 310', 410) also include at least one of disinfection storage reservoirs (360, 360') to collect and reuse the disinfectant for reduced cost and added convenience to the operator.

Figure 7:
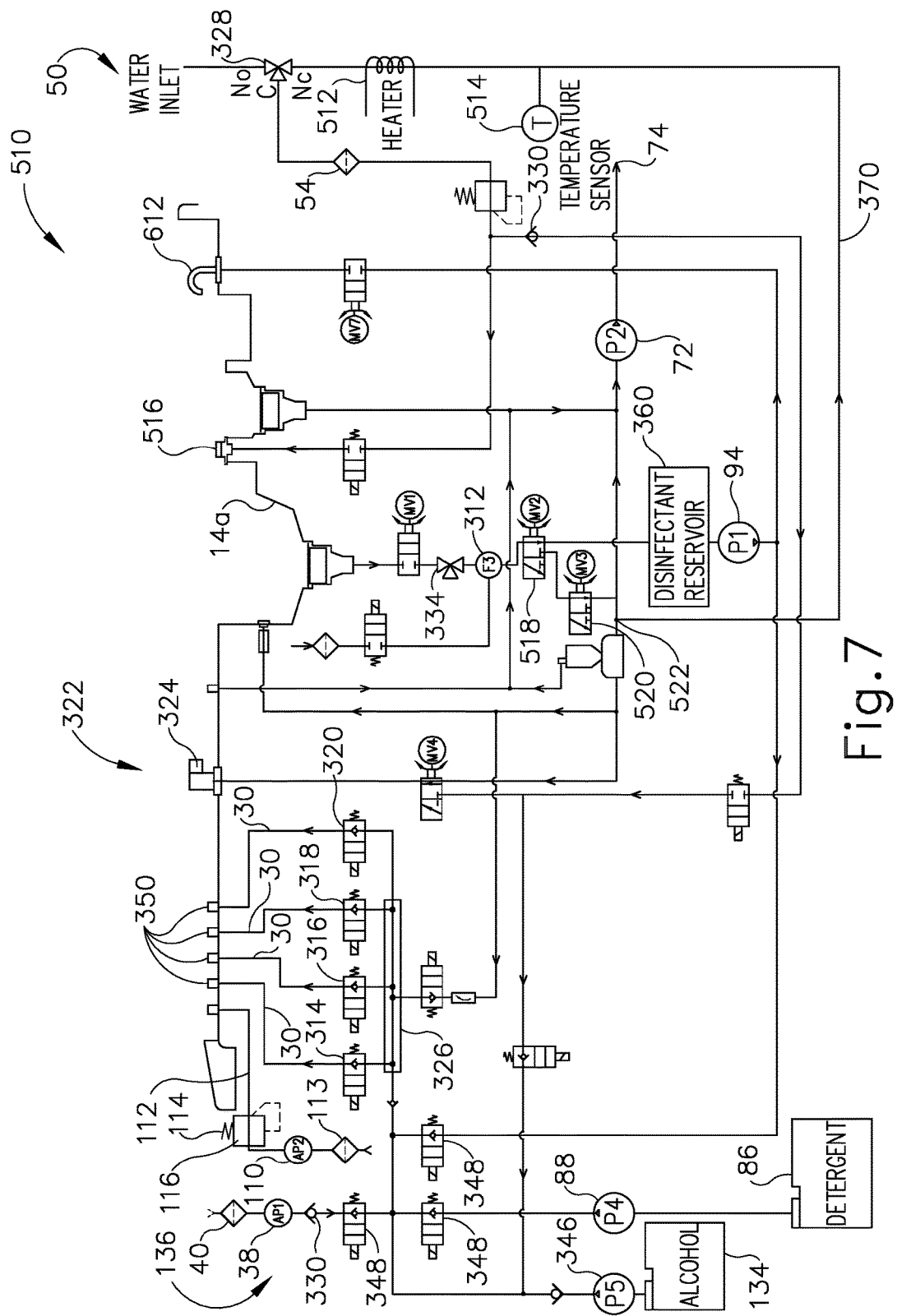
FIG. 7 depicts a schematic diagram of a fifth exemplary reprocessing system.

Further operator convenience is shown and described with respect to a fifth exemplary reprocessing system (510), shown in FIG. 7, which includes a heater (512) and upstream temperature sensor (514) positioned in return flow path (370). By positioning heater (512) and sensor (514) in return flow path (370), temperature sensor (514) accurately senses a minimum fluid temperature in reprocessing system (510) while effectively and conveniently heating the fluid without the necessity for manual manipulation of various valves and conduits by the operator. Alternative versions, such as a sixth exemplary reprocessing system (610) discussed herein with reference to FIG. 8, may also include exemplary return flow path (370), heater (512), and temperature sensor (514). It will be appreciated that various aspects of self-sterilization may be used with respect to any of reprocessing systems (2, 310, 310', 410, 510, 610) and in any combination as described herein.

A. Exemplary Medical Device Reprocessing Apparatus with a Return Flow Path for Self-Disinfection With respect to reprocessing systems (310, 310', 410) shown respectively in FIGS. 4-6, return flow path (370) fluidly connects primary pump (312) to introduction valve (328) as described briefly above for fully circulating fluid, such as disinfectant, throughout reprocessing system (310, 310', 410). Each return flow path (370), which may be more particularly referred to as a self-disinfection flow path in at least some instances, also includes check valve (330) to inhibit fluid, such as water, from flowing backward along return flow path (370) toward primary pump (312). Reprocessing system (310) further includes return valve (344) to further control fluid flowing therealong. By way of example, return valve (344) is configured to transition between an open state and a closed state to respectively allow and inhibit the flow of fluid. Alternatively, return valve (344) may transition to one or more discrete states between the open and closed states for balancing reprocessing system (310) in some desirable, predetermined operation. While return valve (344) may have a variable state, it will be appreciated that such a state, in conjunction with remaining valves (336, 338, 340, 342) may affect operation of reprocessing system (310). The invention described herein is thus not intended to be unnecessarily limited to exemplary return valve (344). For example, alternative reprocessing systems (310', 410) do not include return valve (344) upstream of check valve (330) and, in turn, at least some fluid continuously circulates through reprocessing systems (310', 410).

Introduction valve (328) in each of reprocessing systems (310, 310', 410) shown in FIGS. 4-6 is configured to transition between a supply state and a recirculation state. In the supply state, introduction valve (328) directs all water from water supply (50) toward basin (14a), while inhibiting any fluid from being introduced into the water via return flow path (370). In contrast, introduction valve (328) in the recirculation state inhibits water from water supply (50) from entering reprocessing systems (310, 310', 410), but allows fluid flowing therein via return flow path (370) to be redirected back toward basin (14a) for continued use. While return flow path (370) may generally be used in any cycle for reprocessing endoscope (200) (see FIG. 3), disinfectant storage reservoir (360) in combination with return flow path (370) provides for effective self-disinfection.

B. Exemplary Medical Device Reprocessing Apparatus for Improved Thermal Self-Disinfection FIG. 7 shows exemplary reprocessing system (510) with heater (512) as discussed briefly above. To this end, fluid (e.g., water) is directed via introduction valve (328) toward a water supply nozzle (516) and nozzle assembly (322) for introduction into basin (14a). From basin (14a), the fluid drains through valve (334) and is pumped via primary pump (312) toward flush lines (30) and return flow path (370). Heater (512) is positioned directly upstream from introduction valve (328) for heating fluid (e.g., water) immediately before being recirculated through reprocessing system (510). In addition, temperature sensor (514) measures the temperature of the fluid (e.g., water) immediately upstream of heater (512) prior to being heated to collect a minimum fluid temperature within reprocessing system (510). Heater (512) is configured to heat the fluid (e.g., water) flowing therethrough until the minimum fluid temperature reaches a predetermined temperature, such as a predetermined disinfection temperature that is configured to thermally disinfect reprocessing system (510). In the present example, water is directed along return flow path (370), heated to the predetermined disinfection temperature for self-disinfection, and circulated back through reprocessing system (510) for thermal self-disinfection. However, it should be understood that in some alternative versions heater (512) may be used to heat disinfectant during a self-disinfection cycle.

While reprocessing system (510) shares various similarities with reprocessing systems (2, 310, 310', 410) (see FIGS. 1-6), such as primary pump (312), flush valves (314, 316, 318, 320), and disinfectant storage reservoir (360), reprocessing system (510) of this example also includes at least several distinct features for directing fluid therealong. More particularly, reprocessing system (510) includes an upstream 3-way valve (518) and a downstream 3-way valve (520) that are configured to direct flow to generate the various cycles discussed herein.

Primary pump (312) pumps fluid from basin (14a) directly into upstream valve (518), which directs the fluid toward either disinfectant storage reservoir (360) for collection and reuse or to downstream valve (520). Downstream valve (520) is configured to direct the fluid toward either drain (74) or toward a fluid junction (522), which divides the predetermined supply flow rate of fluid simultaneously along return flow path (370) and into another predetermined supply flow rate directed toward flush lines (30) and nozzle assembly (322).

As shown in FIG. 7, disinfectant storage reservoir (360) is configured to collect disinfectant for use as described above in the disinfection cycle. Disinfectant pump (94) pumps the disinfectant toward manifold (326) to be introduced into the remainder of reprocessing system (510). In fact, the disinfectant flows throughout reprocessing system (510) as divided by fluid junction (522). Of course, reprocessing system (510) is configured to collect the disinfectant at the conclusion of the disinfection and self-disinfection cycles by directing the disinfectant accordingly via upstream valve (518).

Furthermore, with respect to downstream valve (520) and fluid junction (522), primary pump (312) directs the fluid along return flow path (370) toward temperature sensor (514), heater (512), and introduction valve (328) for heating the fluid to the desired temperature. Fluid junction (522) effectively directs the fluid with the predetermined supply flow rate of fluid simultaneously along two general flow paths. The first flow path of fluid reprocesses endoscope (200) in basin (14a), whereas the second flow path of fluid is heated and then mixed back into the fluid flowing through the remainder of reprocessing system (510). In this way, return flow path (370) is always in use with flush lines (30) regardless of whether or not the fluid is being heated for disinfection or self-disinfection. Of course, it will be appreciated that alternative flow paths may be used for directing fluid through an alternatively arranged reprocessing system (510). The invention is thus not intended to be unnecessarily limited to the flow arrangements as described herein.

Figure 8:
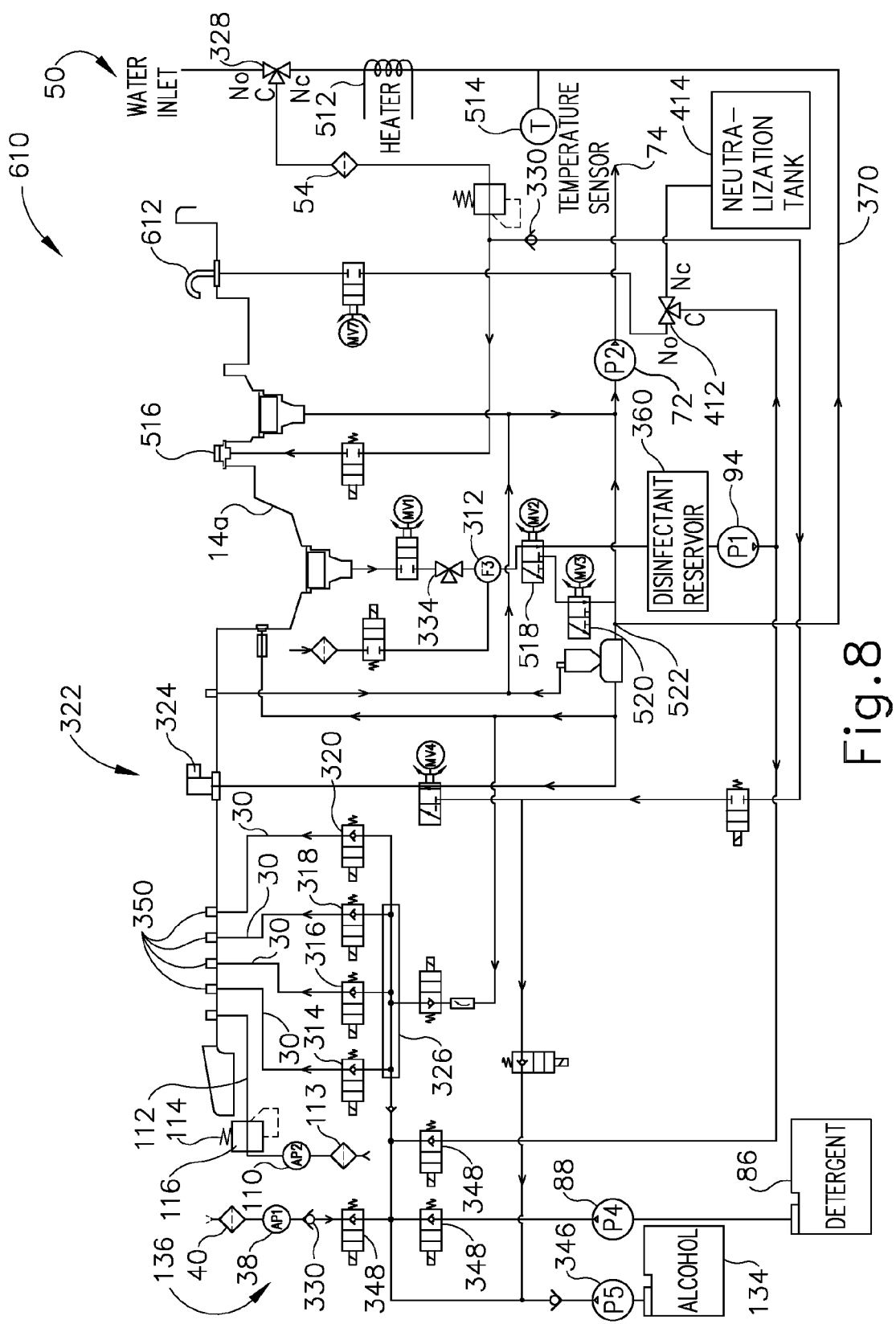
FIG. 8 depicts a schematic diagram of a sixth exemplary reprocessing system.

With respect to FIG. 8, exemplary reprocessing system (610) is similar to reprocessing system (510), but also includes neutralization valve (412) and neutralization tank (414). Specifically, neutralization valve (412) is fluidly connected between a disinfectant spigot (612) and disinfectant pump (94). Disinfectant pump (412) is thereby configured to direct disinfectant from disinfectant storage reservoir (360), through neutralization valve (412), and into neutralization tank (414) for neutralization, removal, and proper disposal.

C. Exemplary Method of Self-Disinfecting a Reprocessing System

In use, reprocessing systems (310, 310', 410) self-disinfect by pumping filtered water in two distinct stages. In a first stage, water is directed from water source (50) and into basin (14a). From basin (14a), the water circulates through heater (80) and is pumped by primary pump (312) only along the self-disinfection path (370), to be returned back to basin (14a) in the present example. The water circulation continues as the water is heated to a predetermined disinfection temperature, thereby disinfecting the water inlet path and reducing the bioburden at filter (54). Once the water reaches the predetermined disinfection temperature, the water continues to circulate for a predetermined amount of time for effective thermal self-disinfection.

Stage two of self-disinfection begins by redirecting the circulating water from the self-disinfection path (370) and toward manifold (326) and the plurality of nozzles (324) for discharge into basin (14a). The water continues to circulate in stage two while continuing to be heated to maintain the predetermined disinfection temperature, thereby thermally disinfecting various components that connect with endoscope (200) (see FIG. 3). After all, in the present example, endoscope (200) is not present in basin (14a) during self-disinfection. The water continues to circulate for another predetermined amount of time in stage two until thermal self-disinfection is complete.

Additional disinfection that may include endoscope (200) (see FIG. 3) is performed by pumping disinfectant from disinfectant storage reservoir (360) and into basin (14a). Primary pump (312) in turn pumps the disinfectant toward the collection of valves (336, 338, 340, 342, 344) such that disinfectant flows through flush lines (30) and nozzle assembly (322) and along return flow path (370). The disinfectant in return flow path (370) is received within introduction valve (328) and circulated back toward basin (14a) with the disinfectant from flush lines (30) and nozzle assembly (322). The disinfectant may then be recirculated for further disinfection or returned to disinfectant storage reservoir (360) upon the completion of chemical disinfection. Heater (80) may also be used to heat the disinfectant for further thermal disinfection during circulation of the disinfectant during self-disinfection.

Reprocessing systems (510, 610) shown in FIGS. 7-8 disinfect by pumping disinfectant from disinfectant storage reservoir (360) and toward flush lines (30) for introduction into basin (14a). Primary pump (312) receives the disinfectant from basin (14a) and pumps the disinfectant through upstream and downstream valves (518, 520) and into fluid junction (522). Fluid junction (522) divides the flow of disinfectant therethrough, with one portion of the flow being directed toward flush lines (30) and nozzle assembly (322), while another portion of the flow is directed along return flow path (370). The disinfectant flows through introduction valve (328) and into basin (14a) with the remaining portion of disinfectant flowing to chemically disinfect the entire reprocessing system (510, 610) that may have contacted endoscope (200) (see FIG. 3) and or waste material removed therefrom.

Thermal disinfection initiates as the fluid flows along return flow path (370) through heater (512), which begins heating the fluid flowing during disinfection. The heated fluid mixes with the cooler fluid in the basin (14a) and through reprocessing system (510, 610) until all of the fluid reaches the predetermined disinfection temperature. Temperature sensor (514), positioned upstream of heater (512), effectively senses the local fluid temperature at its relatively coolest location. Thus, when the measured temperature reaches the predetermined disinfection temperature, the temperature of the remaining fluid is presumed to also be at least at the predetermined disinfection temperature.

While the above description applies to self-disinfection and further disinfection of reprocessing systems (310, 310', 410, 510, 610), it will be appreciated that any fluid may be so circulated for heating and/or reintroduction via introduction valve (328). The return flow path (370) and other various components are thus not intended to be unnecessarily limited to use with water and/or disinfectant in the above described systems.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus for reprocessing a medical device having a first device channel and a second device, the apparatus comprising: (a) a decontamination basin configured to receive the medical device therein; (b) a first flush conduit and a second flush conduit, wherein the first flush conduit has a first coupling port configured to fluidly connect to the first device channel, wherein the second flush conduit has a second coupling port configured to fluidly connect to the second device channel, wherein the first and second flush conduits extend into the decontamination basin such that the first and second coupling ports are configured to be positioned within the decontamination basin; (c) a manifold fluidly connected to the first and second flush conduits, wherein the manifold is configured to distribute the fluid received therein to each of the first and second flush conduits; (d) a primary pump fluidly connected to the manifold and configured to discharge a fluid into the manifold at a predetermined supply flow rate; and (e) a first valve positioned in the first flush conduit in fluid communication with the first flush coupling and a second valve in the second flush conduit in fluid communication with the second flush coupling, wherein the first and second valves are configured to balance the fluid introduced into the manifold at the predetermined supply flow rate such that the fluid discharges from the first and second coupling ports at a first predetermined conduit flow rate and a second predetermined conduit flow rate, respectively, for flushing the first and second device channels during reprocessing of the medical device.

EXAMPLE 2

The apparatus of Example 1, wherein the medical device has a second device channel and a fourth device channel, the apparatus further comprising: (a) a third flush conduit and a fourth flush conduit, wherein the third flush conduit has a third coupling port configured to fluidly connect to the third device channel, wherein the fourth flush conduit has a fourth coupling port configured to fluidly connect to the fourth device channel, wherein the third and fourth flush conduits extend into the decontamination basin such that the third and fourth coupling ports are configured to be positioned within the decontamination basin; (b) the manifold fluidly connected to the third and fourth flush conduits and configured to distribute the fluid received therein to each of the third and fourth flush conduits; and (c) a third valve positioned in the third flush conduit in fluid communication with the third flush coupling and a fourth valve in the fourth flush conduit in fluid communication with the fourth flush coupling, wherein the third and fourth valves are configured to balance the fluid introduced into the manifold at the predetermined supply flow rate such that the fluid discharges from the third and fourth coupling ports at a third predetermined conduit flow rate and a fourth predetermined conduit flow rate, respectively, for flushing the third and fourth device channels during reprocessing of the medical device.

EXAMPLE 3

The apparatus of any one or more of Examples 1 through 2, wherein the first predetermined conduit flow rate and second predetermined conduit flow rate are approximately equivalent.

EXAMPLE 4

The apparatus of any one or more of Examples 1 through 3, further comprising: (a) a nozzle assembly positioned within the decontamination basin and in fluid communication with the primary pump to receive the fluid therefrom, wherein the nozzle assembly is configured to discharge the fluid onto the medical device within the decontamination basin; and (b) a nozzle valve fluidly connected between the nozzle assembly and the primary pump, wherein the nozzle valve is configured to balance the fluid being directed from the primary pump at the predetermined supply flow rate such that the fluid discharges from the nozzle assembly at a predetermined nozzle flow rate during reprocessing of the medical device.

EXAMPLE 5

The apparatus of Example 4, wherein the nozzle assembly includes a plurality of nozzles, and wherein each of the plurality of nozzles is configured to discharge the fluid onto the medical device within the decontamination basin.

EXAMPLE 6

The apparatus of any one or more of Examples 1 through 5, further comprising: (a) an additive storage configured to contain an additive for use with the fluid; and (b) an additive pump configured to pump the additive toward the first and second flush conduits, wherein the additive pump is fluidly connected between the manifold and the primary pump such that the additive pump is configured to introduce the additive into the fluid between the manifold and the primary pump for directing the fluid and the additive collectively toward the first and second flush conduits.

EXAMPLE 7

The apparatus of any one or more of Examples 1 through 6, further comprising: (a) a disinfectant storage reservoir fluidly connected to the decontamination basin and configured to contain a disinfectant; (b) a disinfectant pump in fluid communication between the disinfectant storage reservoir and the decontamination basin, wherein the disinfectant pump is configured to pump the disinfectant from the disinfectant storage reservoir toward the decontamination basin, wherein the primary pump is configured to receive the disinfectant from the decontamination basin and direct the disinfectant along at least one of a circulation phase and a collection phase; and (c) a disinfection valve in fluid communication with each of the decontamination basin, the disinfectant storage reservoir, and the primary pump, wherein the disinfection valve is configured to transition between a circulation state and a collection state, wherein the disinfection valve in the circulation state is configured to direct the disinfectant from the primary pump and toward the decontamination basin in the circulation phase, and wherein the disinfection valve in the collection state is configured to direct the disinfectant from the primary pump and toward the disinfectant storage reservoir, wherein the disinfectant storage reservoir is configured to collect the disinfectant from the primary pump in the collection phase for reuse while reprocessing the medical device.

EXAMPLE 8

The apparatus of Example 7, further comprising: (a) a neutralization valve in fluid communication with the decontamination basin and the disinfectant pump, wherein the neutralization valve is configured to transition between a basin state and a neutralization state; and (b) a neutralization tank fluidly connected to the neutralization valve and configured to neutralize the disinfectant received therein, wherein the neutralization valve in the basin state is configured to direct the disinfectant from the disinfectant pump toward the decontamination basin, and wherein the neutralization valve in the neutralization state is configured to direct the disinfectant from the disinfectant pump toward the neutralization tank for collection therein.

EXAMPLE 9

The apparatus of Example 8, wherein the neutralization valve is fluidly connected between the decontamination basin and the disinfectant pump.

EXAMPLE 10

The apparatus of any one or more of Examples 7 through 9, further comprising: (a) a recirculation conduit in fluid communication with the decontamination basin and configured to receive the fluid directed therefrom; and (b) an introduction valve fluidly connected to the recirculation conduit and configured to fluidly connect to a fluid supply, wherein the introduction valve is in fluid communication with the decontamination basin and configured to transition between a supply state and a recirculation state, wherein the introduction valve in the supply state is configured to receive the fluid from the fluid supply and direct the fluid toward the decontamination basin, and wherein the introduction valve in the recirculation state is configured to receive the fluid from the recirculation conduit and direct the fluid toward the decontamination basin.

EXAMPLE 11

The apparatus of Example 10, further comprising: (a) a temperature sensor positioned within the recirculation conduit and configured to measure a temperature of the disinfectant flowing therethrough; and (b) a heater configured to heat the disinfectant flowing therethrough to a desirable temperature for circulating heated disinfectant toward the decontamination basin with the introduction valve in the recirculation state.

EXAMPLE 12

The apparatus of any one or more of Examples 10 through 11, further comprising a return valve positioned in the recirculation conduit and configured to transition between an open state and a closed state, wherein the return valve in the open state is configured to receive the disinfectant along the recirculation conduit, and wherein the return valve in the closed state is configured to inhibit the disinfectant from flowing along the recirculation conduit and urge the disinfectant toward the manifold.

EXAMPLE 13

The apparatus of any one or more of Examples 10 through 12, wherein the primary pump, the manifold, and the recirculation conduit are in fluid communication such that the pump is configured to simultaneously direct disinfectant along the recirculation conduit and the manifold.

EXAMPLE 14

The apparatus of any one or more of Examples 1 through 13, further comprising a self-disinfection pathway, wherein the self-disinfection pathway is configured to communicate fluid through the apparatus to thereby self-disinfect the apparatus.

EXAMPLE 15

The apparatus of any one or more of Examples 1 through 14, further comprising a heater fluidly connected between the decontamination basin and the primary pump, wherein the heater is configured to heat the fluid flowing therethrough to a predetermined temperature for circulating heated fluid toward the manifold.

EXAMPLE 16

An apparatus for reprocessing a medical device with a disinfectant, comprising: (a) a decontamination basin configured to receive the medical device therein; (b) a disinfectant storage reservoir fluidly connected to the decontamination basin and configured to contain the disinfectant; (c) a disinfectant pump in fluid communication between the disinfectant storage reservoir and the decontamination basin, wherein the disinfectant pump is configured to pump the disinfectant from the disinfectant storage reservoir toward the decontamination basin; (d) a first pump fluidly connected to the decontamination basin and configured to receive the disinfectant therefrom and direct the disinfectant along at least one of a circulation phase or a collection phase; and (e) a disinfection valve in fluid communication with each of the decontamination basin, the disinfectant storage reservoir, and the first pump, wherein the disinfection valve is configured to transition between a circulation state and a collection state, wherein the disinfection valve in the circulation state is configured to direct the disinfectant from the first pump and toward the decontamination basin in the circulation phase, and wherein the disinfection valve in the collection state is configured to direct the disinfectant from the first pump and toward the disinfectant storage reservoir, wherein the disinfectant storage reservoir is configured to collect the disinfectant from the first pump in the collection phase for reuse while reprocessing the medical device.

EXAMPLE 17

The apparatus of Example 16, further comprising: (a) a neutralization valve in fluid communication with the decontamination basin and the disinfectant pump, wherein the neutralization valve is configured to transition between a basin state and a neutralization state; and (b) a neutralization tank fluidly connected to the neutralization valve and configured to neutralize the disinfectant received therein, wherein the neutralization valve in the basin state is configured to direct the disinfectant from the disinfectant pump toward the decontamination basin, and wherein the neutralization valve in the neutralization state is configured to direct the disinfectant from the disinfectant pump toward the neutralization tank for collection therein.

EXAMPLE 18

The apparatus of any one or more of Examples 16 through 17, further comprising: (a) a recirculation conduit in fluid communication with the decontamination basin and configured to receive the fluid directed therefrom; and (b) an introduction valve fluidly connected to the recirculation conduit and configured to fluidly connect to a fluid supply, wherein the introduction valve is in fluid communication with the decontamination basin and is configured to transition between a supply state and a recirculation state, wherein the introduction valve in the supply state is configured to receive the fluid from the fluid supply and direct the fluid toward the decontamination basin, and wherein the introduction valve in the recirculation state is configured to receive the fluid from the recirculation conduit and direct the fluid toward the decontamination basin

EXAMPLE 19

The apparatus of Example 18, further comprising: (a) a temperature sensor positioned within the recirculation conduit and configured to measure a temperature of the disinfectant flowing therethrough; and (b) a heater configured to heat the disinfectant flowing therethrough to a desirable temperature for circulating heated disinfectant toward the decontamination basin with the introduction valve in the recirculation state

EXAMPLE 20

A method of reprocessing a medical device having a first channel and a second channel extending therethrough, comprising: (a) pumping a primary fluid flow with a predetermined supply flow rate from a pump into a manifold having a first flush conduit and a second flush conduit in fluid communication therewith; (b) directing a first fluid flow from the primary fluid flow and into a first valve along the first flush conduit; (c) directing a second fluid flow from the primary fluid flow and into a second valve along the second flush conduit; (d) balancing the first and second fluid flows with the first and second valves such that the first fluid flow has a first predetermined conduit flow rate and the second fluid flow has a second predetermined conduit flow rate; and (e) discharging the first and second fluid flows with the first and second predetermined conduit flow rates into the respective first and second channels of the medical device for reprocessing the medical device.

VII. Miscellaneous

It should be understood that any of the teachings herein may be readily combined with the teachings of U.S. patent application Ser. No. 15/157,650, entitled "Apparatus and Method to Identify Endoscope Type and Provide Tailored Reprocessing," filed on May 18, 2016, published as U.S. Pub. No. 2017/0332891 on Nov. 23, 2017, the disclosure of which is incorporated by reference herein. In particular, the systems described herein may be readily modified to incorporate the features taught in U.S. Pub. No. 2017/0332891. Various suitable ways in which the teachings herein may be combined with the teachings of U.S. Pub. No. 2017/0332891, will be apparent to those of ordinary skill in the art.

Similarly, it should be understood that any of the teachings herein may be readily combined with the teachings of U.S. patent application Ser. No. 15/157,952, entitled "Apparatus and Method to Measure Concentration of Disinfectant in Medical Device Reprocessing System," filed on May 18, 2016, published as U.S. Pub. No. 2017/0333584 on Nov. 23, 2017, the disclosure of which is incorporated by reference herein. In particular, the systems described herein may be readily modified to incorporate the features taught in U.S. Pub. No. 2017/0333584. Various suitable ways in which the teachings herein may be combined with the teachings of U.S. Pub. No. 2017/0333584, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for reprocessing a medical device having a first device channel and a second device channel, the apparatus comprising:
(a) a decontamination basin configured to receive the medical device therein;
(b) a first flush conduit and a second flush conduit, wherein the first flush conduit has a first coupling port configured to fluidly connect to the first device channel, wherein the second flush conduit has a second coupling port configured to fluidly connect to the second device channel, wherein the first and second flush conduits extend into the decontamination basin such that the first and second coupling ports are configured to be positioned within the decontamination basin;

(c) a manifold fluidly connected to the first and second flush conduits, wherein the manifold is configured to distribute the fluid received therein to each of the first and second flush conduits;

(d) a primary pump fluidly connected to the manifold and configured to discharge a fluid into the manifold at a predetermined supply flow rate;

(e) a first valve positioned in the first flush conduit in fluid communication with the first flush coupling and a second valve in the second flush conduit in fluid communication with the second flush coupling, wherein the first and second valves are configured to balance the fluid introduced into the manifold at the predetermined supply flow rate such that the fluid discharges from the first and second coupling ports at a first predetermined conduit flow rate and a second predetermined conduit flow rate, respectively, for flushing the first and second device channels during reprocessing of the medical device;

(f) an additive storage configured to contain an additive for use with the fluid; and (g) an additive pump configured to pump the additive toward the first and second flush conduits, wherein the additive pump is fluidly connected between upstream of the manifold and downstream of the primary pump such that the additive pump is configured to introduce the additive into the fluid between the manifold and the primary pump for directing the fluid and the additive collectively toward the first and second flush conduits.

2. The apparatus of claim 1, wherein the medical device has a third device channel and a fourth device channel, the apparatus further comprising:

(a) a third flush conduit and a fourth flush conduit, wherein the third flush conduit has a third coupling port configured to fluidly connect to the third device channel, wherein the fourth flush conduit has a fourth coupling port configured to fluidly connect to the fourth device channel, wherein the third and fourth flush conduits extend into the decontamination basin such that the third and fourth coupling ports are configured to be positioned within the decontamination basin;

(b) the manifold fluidly connected to the third and fourth flush conduits and configured to distribute the fluid received therein to each of the third and fourth flush conduits; and (c) a third valve positioned in the third flush conduit in fluid communication with the third flush coupling and a fourth valve in the fourth flush conduit in fluid communication with the fourth flush coupling, wherein the third and fourth valves are configured to balance the fluid introduced into the manifold at the predetermined supply flow rate such that the fluid discharges from the third and fourth coupling ports at a third predetermined conduit flow rate and a fourth predetermined conduit flow rate, respectively, for flushing the third and fourth device channels during reprocessing of the medical device.

3. The apparatus of claim 1, wherein the first predetermined conduit flow rate and second predetermined conduit flow rate are approximately equivalent.

4. The apparatus of claim 1, further comprising:

(a) a nozzle assembly positioned within the decontamination basin and in fluid communication with the primary pump to receive the fluid therefrom, wherein the nozzle assembly is configured to discharge the fluid onto the medical device within the decontamination basin; and (b) a nozzle valve fluidly connected between the nozzle assembly and the primary pump, wherein the nozzle valve is configured to balance the fluid being directed from the primary pump at the predetermined supply flow rate such that the fluid discharges from the nozzle assembly at a predetermined nozzle flow rate during reprocessing of the medical device.

5. The apparatus of claim 4, wherein the nozzle assembly includes a plurality of nozzles, and wherein each of the plurality of nozzles is configured to discharge the fluid onto the medical device within the decontamination basin.

6. The apparatus of claim 1, further comprising:

(a) a disinfectant storage reservoir fluidly connected to the decontamination basin and configured to contain a disinfectant;

(b) a disinfectant pump in fluid communication between the disinfectant storage reservoir and the decontamination basin, wherein the disinfectant pump is configured to pump the disinfectant from the disinfectant storage reservoir toward the decontamination basin, wherein the primary pump is configured to receive the disinfectant from the decontamination basin and direct the disinfectant along at least one of a circulation phase and a collection phase; and (c) a disinfection valve in fluid communication with each of the decontamination basin, the disinfectant storage reservoir, and the primary pump, wherein the disinfection valve is configured to transition between a circulation state and a collection state, wherein the disinfection valve in the circulation state is configured to direct the disinfectant from the primary pump and toward the decontamination basin in the circulation phase, and wherein the disinfection valve in the collection state is configured to direct the disinfectant from the primary pump and toward the disinfectant storage reservoir, wherein the disinfectant storage reservoir is configured to collect the disinfectant from the primary pump in the collection phase for reuse while reprocessing the medical device.

7. The apparatus of claim 6, further comprising:

(a) a neutralization valve in fluid communication with the decontamination basin and the disinfectant pump, wherein the neutralization valve is configured to transition between a basin state and a neutralization state; and (b) a neutralization tank fluidly connected to the neutralization valve and configured to neutralize the disinfectant received therein, wherein the neutralization valve in the basin state is configured to direct the disinfectant from the disinfectant pump toward the decontamination basin, and wherein the neutralization valve in the neutralization state is configured to direct the disinfectant from the disinfectant pump toward the neutralization tank for collection therein.

8. The apparatus of claim 7, wherein the neutralization valve is fluidly connected between the decontamination basin and the disinfectant pump.

9. The apparatus of claim 6, further comprising:
(a) a recirculation conduit in fluid communication with the decontamination basin and configured to receive the fluid directed therefrom; and
(b) an introduction valve fluidly connected to the recirculation conduit and configured to fluidly connect to a fluid supply, wherein the introduction valve is in fluid communication with the decontamination basin and configured to transition between a supply state and a recirculation state,
wherein the introduction valve in the supply state is configured to receive the fluid from the fluid supply and direct the fluid toward the decontamination basin, and
wherein the introduction valve in the recirculation state is configured to receive the fluid from the recirculation conduit and direct the fluid toward the decontamination basin.

10. The apparatus of claim 9, further comprising:
(a) a temperature sensor positioned within the recirculation conduit and configured to measure a temperature of the disinfectant flowing therethrough; and
(b) a heater configured to heat the disinfectant flowing therethrough to a desirable temperature for circulating heated disinfectant toward the decontamination basin with the introduction valve in the recirculation state.

11. The apparatus of claim 9, further comprising a return valve positioned in the recirculation conduit and configured to transition between an open state and a closed state, wherein the return valve in the open state is configured to receive the disinfectant along the recirculation conduit, and wherein the return valve in the closed state is configured to inhibit the disinfectant from flowing along the recirculation conduit and urge the disinfectant toward the manifold.

12. The apparatus of claim 9, wherein the primary pump, the manifold, and the recirculation conduit are in fluid communication such that the pump is configured to simultaneously direct disinfectant along the recirculation conduit and the manifold.

13. The apparatus of claim 1, further comprising a self-disinfection pathway, wherein the self-disinfection pathway is configured to communicate fluid through the apparatus to thereby self-disinfect the apparatus.

14. The apparatus of claim 1, further comprising a heater fluidly connected between the decontamination basin and the primary pump, wherein the heater is configured to heat the fluid flowing therethrough to a predetermined temperature for circulating heated fluid toward the manifold.

15. The apparatus of claim 1, further comprising a drain fluidly connected to the primary pump such that the primary pump is configured to pump the fluid from the decontamination basin and toward the drain.

16. The apparatus of claim 1, further comprising a disinfectant storage reservoir fluidly connected to the decontamination basin and configured to contain a disinfectant, wherein the primary pump is fluidly connected to the disinfectant storage reservoir and configured to direct the disinfectant from the decontamination basin and into the disinfectant storage reservoir.

17. The apparatus of claim 13, further comprising an introduction valve and an inlet path, wherein the introduction valve is configured to receive water from a water source, wherein the inlet path fluidly connects the introduction valve to the decontamination basin, and wherein the self-disinfection pathway also fluidly connects to the introduction valve such that the introduction valve is further configured to receive fluid from the self-disinfection pathway to thereby self-disinfect the inlet path.

18. An apparatus for reprocessing a medical device having a first device channel and a second device channel, the apparatus comprising:
(a) a decontamination basin configured to receive the medical device therein;
(b) a first flush conduit and a second flush conduit, wherein the first flush conduit has a first coupling port configured to fluidly connect to the first device channel, wherein the second flush conduit has a second coupling port configured to fluidly connect to the second device channel, wherein the first and second flush conduits extend into the decontamination basin such that the first and second coupling ports are configured to be positioned within the decontamination basin;
(c) a manifold fluidly connected to the first and second flush conduits, wherein the manifold is configured to distribute the fluid received therein to each of the first and second flush conduits;
(d) a primary pump fluidly connected to the manifold and configured to discharge a fluid into the manifold at a predetermined supply flow rate;
(e) a first valve positioned in the first flush conduit in fluid communication with the first flush coupling and a second valve in the second flush conduit in fluid communication with the second flush coupling, wherein the first and second valves are configured to balance the fluid introduced into the manifold at the predetermined supply flow rate such that the fluid discharges from the first and second coupling ports at a first predetermined conduit flow rate and a second predetermined conduit flow rate, respectively, for flushing the first and second device channels during reprocessing of the medical device;
(f) a disinfectant storage reservoir fluidly connected to the decontamination basin and configured to contain a disinfectant, wherein the primary pump is fluidly connected to the disinfectant storage reservoir and configured to direct the disinfectant from the decontamination basin and into the disinfectant storage reservoir.

19. The apparatus of claim 18, further comprising:
(a) a disinfectant pump in fluid communication between the disinfectant storage reservoir and the decontamination basin, wherein the disinfectant pump is configured to pump the disinfectant from the disinfectant storage reservoir toward the decontamination basin, wherein the primary pump is configured to receive the disinfectant from the decontamination basin and direct the disinfectant along at least one of a circulation phase and a collection phase; and
(b) a disinfection valve in fluid communication with each of the decontamination basin, the disinfectant storage reservoir, and the primary pump, wherein the disinfection valve is configured to transition between a circulation state and a collection state, wherein the disinfection valve in the circulation state is configured to direct the disinfectant from the primary pump and toward the decontamination basin in the circulation phase, and wherein the disinfection valve in the collection state is configured to direct the disinfectant from the primary pump and toward the disinfectant storage reservoir,
wherein the disinfectant storage reservoir is configured to collect the disinfectant from the primary pump in the collection phase for reuse while reprocessing the medical device.

20. An apparatus for reprocessing a medical device having a first device channel and a second device channel, the apparatus comprising:
  (a) a decontamination basin configured to receive the medical device therein;
  (b) a first flush conduit and a second flush conduit, wherein the first flush conduit has a first coupling port configured to fluidly connect to the first device channel, wherein the second flush conduit has a second coupling port configured to fluidly connect to the second device channel, wherein the first and second flush conduits extend into the decontamination basin such that the first and second coupling ports are configured to be positioned within the decontamination basin;
  (c) a manifold fluidly connected to the first and second flush conduits, wherein the manifold is configured to distribute the fluid received therein to each of the first and second flush conduits;
  (d) a primary pump fluidly connected to the manifold and configured to discharge a fluid into the manifold at a predetermined supply flow rate;
  (e) a first valve positioned in the first flush conduit in fluid communication with the first flush coupling and a second valve in the second flush conduit in fluid communication with the second flush coupling, wherein the first and second valves are configured to balance the fluid introduced into the manifold at the predetermined supply flow rate such that the fluid discharges from the first and second coupling ports at a first predetermined conduit flow rate and a second predetermined conduit flow rate, respectively, for flushing the first and second device channels during reprocessing of the medical device;
  (f) an introduction valve configured to receive water from a water source;
  (g) an inlet path fluidly connecting the introduction valve to the decontamination basin; and
  (h) a self-disinfection pathway fluidly connected downstream of the primary pump, wherein the self-disinfection pathway fluidly connects the primary pump to the introduction valve such that the introduction valve is further configured to receive fluid from the self-disinfection pathway to thereby self-disinfect the inlet path, wherein the self-disinfection pathway and the manifold are respectively in parallel fluid communication with the decontamination basin.

* * * * *